United States Patent [19]
Beck et al.

[11] Patent Number: 6,124,463
[45] Date of Patent: Sep. 26, 2000

[54] BENZIMIDAZOLES AS CORTICOTROPIN RELEASE FACTOR ANTAGONISTS

[75] Inventors: James Peter Beck, Smyrna, Del.; Matthew Allen Curry, Coatesville, Pa.

[73] Assignee: DuPont Pharmaceuticals, Wilmington, Del.

[21] Appl. No.: 09/333,161

[22] Filed: Jun. 14, 1999

Related U.S. Application Data

[60] Provisional application No. 60/091,575, Jul. 2, 1998.

[51] Int. Cl.[7] .................. C07D 401/02; C07D 401/04; C07D 235/20; C07D 235/18; A61K 31/44; A61K 31/4184; A61K 25/28

[52] U.S. Cl. ............................ 546/273.4; 548/301.1; 548/304.4; 548/310.4; 514/339; 514/394; 544/333; 546/273.7

[58] Field of Search ................ 548/301.1, 304.4, 548/310.4, 247; 514/394, 339; 544/333; 546/273.4, 273.7

[56] References Cited

U.S. PATENT DOCUMENTS

| | | | |
|---|---|---|---|
| 4,797,399 | 1/1989 | Ueda et al. | 514/253 |
| 5,015,473 | 5/1991 | Chen | 424/114 |
| 5,075,311 | 12/1991 | Hubsch et al. | 514/258 |
| 5,102,880 | 4/1992 | Chakravarty et al. | 514/212 |
| 5,128,327 | 7/1992 | Chakravarty et al. | 514/81 |
| 5,145,959 | 9/1992 | Hubsch et al. | 544/279 |
| 5,157,026 | 10/1992 | Chakravarty et al. | 514/81 |
| 5,171,353 | 12/1992 | Fischer et al. | 71/92 |
| 5,176,991 | 1/1993 | Jones et al. | 430/569 |
| 5,178,997 | 1/1993 | Maskasky et al. | 430/569 |
| 5,183,732 | 2/1993 | Maskasky | 430/569 |
| 5,185,239 | 2/1993 | Maskasky | 430/569 |
| 5,187,159 | 2/1993 | Greenlee et al. | 514/81 |
| 5,250,408 | 10/1993 | Chang et al. | 430/569 |
| 5,250,531 | 10/1993 | Cooper | 514/256 |
| 5,260,322 | 11/1993 | Nakasima et al. | 514/341 |
| 5,272,052 | 12/1993 | Maskasky | 430/569 |
| 5,312,820 | 5/1994 | Ashton et al. | 514/227.5 |
| 5,319,080 | 6/1994 | Leumann | 536/27.1 |
| 5,330,989 | 7/1994 | Soll et al. | 514/25 |
| 5,332,814 | 7/1994 | Moser | 544/229 |
| 5,332,820 | 7/1994 | Duncia | 546/118 |
| 5,338,740 | 8/1994 | Carpino et al. | 514/259 |
| 5,338,756 | 8/1994 | Fortin et al. | 514/394 |
| 5,374,638 | 12/1994 | Dhanoa et al. | 514/326 |
| 5,376,665 | 12/1994 | Miyata et al. | 514/301 |
| 5,376,666 | 12/1994 | Duncia | 514/303 |
| 5,385,925 | 1/1995 | Narr et al. | 514/382 |
| 5,389,509 | 2/1995 | Maskasky | 430/567 |

(List continued on next page.)

FOREIGN PATENT DOCUMENTS

| | | |
|---|---|---|
| 96-72147 | 4/1997 | Australia . |
| 97-26365 | 10/1997 | Australia . |
| 2011222 | 9/1990 | Canada . |
| 2024137 | 3/1991 | Canada . |
| 2032831 | 6/1991 | Canada . |
| 2062558 | 9/1992 | Canada . |
| 2080640 | 10/1992 | Canada . |
| 2089689 | 2/1993 | Canada . |
| 2099712 | 6/1993 | Canada . |
| 2158996 | 10/1994 | Canada . |
| 2147798 | 4/1995 | Canada . |
| 0345747A2 | 12/1989 | European Pat. Off. . |
| 0399731B1 | 11/1990 | European Pat. Off. . |
| 0400974A2 | 12/1990 | European Pat. Off. . |
| 0416740A2 | 3/1991 | European Pat. Off. . |
| 0434038A1 | 6/1991 | European Pat. Off. . |
| 0445467A1 | 9/1991 | European Pat. Off. . |
| 0466711B1 | 1/1992 | European Pat. Off. . |
| 0480204A1 | 4/1992 | European Pat. Off. . |
| 0533189A1 | 9/1992 | European Pat. Off. . |
| 0520423A2 | 12/1992 | European Pat. Off. . |
| 0353902B1 | 5/1993 | European Pat. Off. . |
| 0542681A1 | 5/1993 | European Pat. Off. . |
| 0584811A1 | 8/1993 | European Pat. Off. . |
| 0584817A1 | 8/1993 | European Pat. Off. . |
| 074174A2 | 12/1993 | European Pat. Off. . |
| 0577558A2 | 1/1994 | European Pat. Off. . |
| 0584817B1 | 4/1996 | European Pat. Off. . |
| 0706795A2 | 4/1996 | European Pat. Off. . |
| 0345747B1 | 6/1996 | European Pat. Off. . |
| 0718674A1 | 6/1996 | European Pat. Off. . |
| 05584811B1 | 10/1996 | European Pat. Off. . |

(List continued on next page.)

OTHER PUBLICATIONS

Mataka et al, Reduction of 4,7–Diphenyl–1,2,5–thia(oxa)diazolo[3,4–c]pyridines Affording 2,5–Diphenyl–3,4–diaminopyridines and Ring Closure of the Diamines to Fluorescent Azaheterocycles, *Jrnl of Heterocyclic Chem.*, 19/6, 1481–1488, (1982).

Kalme et al, Nucleophilic Substitution in . . . , Khim Geterotsikl Soedin, 12, 1646–1650, (1992).

Kiyama et al., Synthesis and Evaluation of Novel Nonpeptide Angiotensin II Receptor Antagonists . . . , *Chem. Pharm Bull.*, 43/3, 450–460, (1995).

Yashioka et al., New Synthetic Route to Imidazo[4,5–c] Pyridines By The Thermal Electrocycli Reaction of 1–Azahexatriene, Hetercycles, Vol. 41, No.1, 161 (1995).

Unknown, Mixtures of Perylene–Pigments For Use In A Photoconductive Element, Research Disclosure, Oct. 1991.

*Primary Examiner*—Floyd D. Higel
*Attorney, Agent, or Firm*—Monte R. Browder; Kenneth B. Rubin

[57] ABSTRACT

The present invention describes novel benzimidazoles of formula:

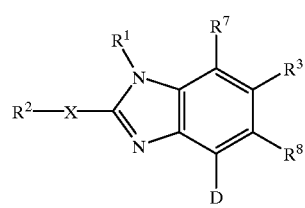

or pharmaceutically acceptable salt forms thereof, which are useful as CRF antagonists.

8 Claims, No Drawings

U.S. PATENT DOCUMENTS

| | | | |
|---|---|---|---|
| 5,389,634 | 2/1995 | Fortin et al. | 514/248 |
| 5,389,641 | 2/1995 | Naka et al. | 514/303 |
| 5,393,878 | 2/1995 | Leumann | 536/28.2 |
| 5,395,840 | 3/1995 | Miiler et al. | 514/300 |
| 5,424,432 | 6/1995 | Fredenburgh et al. | 546/118 |
| 5,428,168 | 6/1995 | Whittaker et al. | 546/118 |
| 5,434,150 | 7/1995 | Austel et al. | 514/228.5 |
| 5,444,068 | 8/1995 | Heitsch et al. | 514/303 |
| 5,446,159 | 8/1995 | Stucky et al. | 546/118 |
| 5,446,160 | 8/1995 | Stucky et al. | 546/110 |
| 5,459,147 | 10/1995 | Hauel et al. | 514/303 |
| 5,470,867 | 11/1995 | Fortin et al. | 514/393 |
| 5,498,715 | 3/1996 | Kuo et al. | 546/118 |
| 5,514,682 | 5/1996 | Street | 514/266 |
| 5,541,324 | 7/1996 | TenBrink et al. | 544/346 |
| 5,565,437 | 10/1996 | Marquez et al. | 514/45 |
| 5,580,981 | 12/1996 | Carpino | 544/262 |
| 5,587,393 | 12/1996 | Narr et al. | 514/381 |
| 5,587,470 | 12/1996 | Cook et al. | 536/23.1 |
| 5,597,826 | 1/1997 | Howard et al. | 514/255 |
| 5,635,525 | 6/1997 | Heitsch et al. | 514/394 |
| 5,684,029 | 11/1997 | Narr et al. | 514/394 |

FOREIGN PATENT DOCUMENTS

| | | |
|---|---|---|
| 0773023A1 | 5/1997 | European Pat. Off. |
| 0812831A1 | 12/1997 | European Pat. Off. |
| 0839813A1 | 5/1998 | European Pat. Off. |
| 9212167 | 10/1992 | France |
| 3921271A | 1/1991 | Germany |
| 42 30 464A1 | 9/1992 | Germany |
| 4208535A | 9/1992 | Germany |
| 5-213754 | of 0000 | Japan |
| 5-287209 | of 0000 | Japan |
| 9-160166 | 6/1997 | Japan |
| 2263637A | 8/1993 | United Kingdom |
| 2272899A | 6/1994 | United Kingdom |
| WO88/03025 | 5/1988 | WIPO |
| WO91/19715 | 12/1991 | WIPO |
| WO92/22552 | 12/1992 | WIPO |
| WO93/03033 | 2/1993 | WIPO |
| WO93/23396 | 11/1993 | WIPO |
| WO94/10171 | 5/1994 | WIPO |
| WO94/12461 | 6/1994 | WIPO |
| WO94/18215 | 8/1994 | WIPO |
| WO94/22859 | 10/1994 | WIPO |
| WO95/10506 | 4/1995 | WIPO |
| WO95/20597 | 8/1995 | WIPO |
| WO95/21836 | 8/1995 | WIPO |
| WO95/21838 | 8/1995 | WIPO |
| WO95/33727 | 12/1995 | WIPO |
| WO95/33750 | 12/1995 | WIPO |
| WO95/34563 | 12/1995 | WIPO |
| WO95/34564 | 12/1995 | WIPO |
| WO96/01624 | 1/1996 | WIPO |
| WO96/02535A1 | 2/1996 | WIPO |
| WO96/17076 | 6/1996 | WIPO |
| WO96/17077 | 6/1996 | WIPO |
| WO96/19478 | 6/1996 | WIPO |
| WO96/24338 | 8/1996 | WIPO |
| WO96/24375 | 8/1996 | WIPO |
| WO97/08150 | 3/1997 | WIPO |
| WO97/37993 | 10/1997 | WIPO |
| WO98/08847 | 3/1998 | WIPO |
| WO98/35967 | 8/1998 | WIPO |
| WO 99/01454 | 1/1999 | WIPO |
| WO 99/63394 | 11/1999 | WIPO |

BENZIMIDAZOLES AS CORTICOTROPIN RELEASE FACTOR ANTAGONISTS

This application is a continuation of provisional patent application Ser. No. 60/091,575 filed on Jul. 2, 1998.

FIELD OF THE INVENTION

This invention relates to novel benzimidazoles, pharmaceutical compositions containing the same and methods of using same in the treatment of psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing corticotropin releasing factor (CRF), including but not limited to disorders induced or facilitated by CRF.

BACKGROUND

Corticotropin releasing factor, a 41 amino acid peptide, is the primary physiological regulator of proopiomelanocortin (POMC)-derived peptide secretion from the anterior pituitary gland [J. Rivier et al., *Proc. Nat. Acad. Sci.* (USA) 80:4851 (1983); W. Vale et al., *Science* 213:1394 (1981)]. In addition to its endocrine role at the pituitary gland, immunohisto-chemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provides evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines [C. W. Berridge and A. J. Dunn, *Horm. Behav.* 21:393 (1987), Brain Research Reviews 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Rol5-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

In view of the above, efficacious and specific antagonists of CRF are desired as potentially valuable therapeutic agents for the treatment of psychiatric disorders and neurological diseases. It is thus desirable to discover new CRF antagonists.

SUMMARY OF THE INVENTION

Accordingly, one object of the present invention is to provide novel benzimidazoles which are useful as CRF antagonists or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt form thereof.

It is another object of the present invention to provide a method for treating psychiatric disorders and neurological diseases comprising administering to a host in need of such treatment a therapeutically effective amount of at least one of the compounds of the present invention or a pharmaceutically acceptable salt form thereof.

These and other objects, which will become apparent during the following detailed description, have been achieved by the inventors, discovery that compounds of formula I:

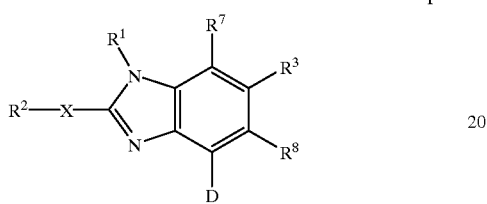

or pharmaceutically acceptable salt forms thereof, wherein $R^1$, $R^2$, $R^3$, $R^7$, $R^8$, X and D are defined below, are CRF antagonists.

DETAILED DESCRIPTION OF THE INVENTION

[1] Thus, in a first embodiment, the present invention provides a novel compound of formula I:

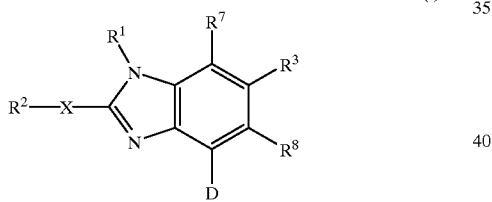

or a stereoisomer or pharmaceutically acceptable salt form thereof, wherein:

D is an aryl or heteroaryl group attached through an unsaturated carbon atom;

X is selected from the group CH—$R^9$, N—$R^{10}$, O, S(O)$_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$—$C_{1-10}$ alkyl, —$SO_2$—$R^{1a}$ and —$SO_2$—$R^{1b}$;

$R^1$ is substituted with 0–1 substituents selected from the group —CN, —S(O)$_n R^{14b}$, —COR$^{13a}$, —CO$_2 R^{13a}$, —NR$^{15a}$COR$^{13a}$, —N(COR$^{13a}$)$_2$, —NR$^{15a}$CONR$^{13a}R^{16a}$, —NR$^{15a}$CO$_2 R^{14b}$, —CONR$^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —S(O)$_n$—, —NR$^{13a}$—, —NCO$_2 R^{14b}$—, —NCOR$^{14b}$— and —NSO$_2 R^{14b}$—, and wherein N$_4$ in 1-piperazinyl is substituted with 0–1 substituents selected from the group R$^{13a}$, CO$_2 R^{14b}$, COR$^{14b}$ and SO$_2 R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, —NR$^{13a}R^{16a}$, $C_{1-4}$ alkoxy-$C_{1-4}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl—(CH$_2$)$_2$— group;

$R^{1a}$ is aryl and is selected from the group phenyl, naphthyl, indanyl and indenyl, each R1a being substituted with 0–1 —OR$^{17}$ and 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, SH, —S(O)$_n R^{18}$, —COR$^{17}$, —OC(O)R$^{18}$, —NR$^{15a}$COR$^{17}$, —N(COR$^{17}$)$_2$, —NR$^{15a}$CONR$^{17a}R^{19a}$, —NR$^{15a}$CO$_2 R^8$, —NR$^{17a}R^{19a}$, and —CONR$^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{17}$, SH, —S(O)$_m R^{18}$, —COR$^{17}$, —OC(O)R$^{18}$, —NR$^{15a}$COR$^{17}$, —N(COR$^{17}$)$_2$, —NR$^{15a}$CONR$^{17a}R^{19a}$, —NR$^{15a}$CO$_2 R^{18}$, —NR$^{17a}R^{19a}$, and —CONR$^{17a}R^{19a}$ and each heteroaryl being substituted on any nitrogen atom with 0–1 substituents selected from the group $R^{15a}$, CO$_2 R^{14b}$, COR$^{14b}$ and SO$_2 R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR$^{13a}$, SH, —S(O)$_n R^{14b}$, —COR$^{13a}$, —OC(O)R$^{14b}$, —NR$^{15a}$COR$^{13a}$, —N(COR$^{13a}$)$_2$, —NR$^{15a}$CONR$^{13a}R^{16a}$, —NR$^{15a}$CO$_2 R^{14b}$, —NR$^{13a}R^{16a}$, and —CONR$^{13a}R^{16a}$ and each heterocyclyl being substituted on any nitrogen atom with 0–1 substituents selected from the group $R^{13a}$, CO$_2 R^{14b}$, COR$^{14b}$ and SO$_2 R^{14b}$ and wherein any sulfur atom is optionally monooxidized or dioxidized;

provided that $R^1$ is other than a —(CH$_2$)$_{1-4}$-aryl, —(CH$_2$)$_{1-4}$-heteroaryl, or —(CH$_2$)$_{1-4}$-heterocycle, wherein the aryl, heteroaryl, or heterocycle group is substituted or unsubstituted;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where x is a bond, is selected from the group —CN, CF$_3$ and C$_2$F$_5$;

$R^3$, $R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $(C_{1-4}$ alkyl$)_{2a}$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl$)_2$amino; provided that when $R^1$ is unsubstituted $C_{1-10}$ alkyl, then $R^3$ is other than substituted or unsubstituted phenyl;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl ($C_{1-4}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl;

heteroaryl is independently selected at each occurence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$; and, provided that when D is imidazole or triazole, $R^1$ is other than unsubstituted $C_{1-6}$ linear or branched alkyl or $C_{3-6}$ cycloalkyl.

[2a] In a more preferred embodiment, the present invention provides a novel compound of formula I, wherein:

X is selected from the group O, $S(O)_n$ and a bond;

n is 0, 1 or 2;

$R^1$ is selected from the group $C_{1-6}$ alkyl, $C_{2-6}$ alkenyl, $C_{2-6}$ alkynyl, $C_{3-8}$ cycloalkyl, $C_{3-8}$ cycloalkyl-$C_{16}$ alkyl;

$R^1$ is substituted with 0–1 substituents selected from the group —CN, —$S(O)_nR^{14b}$, —$COR^{13a}$, —$CO_2R^{13a}$, and $C_{3-8}$ cycloalkyl, wherein 0–1 carbon atoms in the $C_{4-8}$ cycloalkyl is replaced by a group selected from the group —O—, —$S(O)_n$—, —$NR^{13a}$—, —$NCO_2R^{14b}$—, —$NCOR^{14b}$— and —$NSO_2R^{14b}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, $CF_2CF_3$, —$OR^{13a}$, —$NR^{13a}R^{16a}$, $C_{1-2}$ alkoxy-$C_{1-2}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl—$(CH_2)_2$— group;

$R^{1a}$ is aryl and is selected from the group phenyl and indanyl, each $R^{1a}$ being substituted with 0–1 —$OR^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —S(O)$_n$R$^{18}$, —COR$^{17}$, —NR$^{17a}$R$^{19a}$, and CONR$^{17a}$R$^{19a}$;

R$^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, CF$_3$, —CN, —OR$^{17}$, —S(O)$_m$R$^{18}$, —COR$^{17}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

provided that R$^1$ is other than a —(CH$_2$)$_{1-4}$-aryl or —(CH$_2$)$_{1-4}$-heteroaryl wherein the aryl or heteroaryl group is substituted or unsubstituted;

R$^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

R$^3$, R$^7$ and R$^8$ are independently selected at each occurrence from the group H, Br, Cl, F, —CN, $C_{1-4}$ alkyl, $C_{3-6}$ cycloalkyl, $C_{1-4}$ alkoxy, NH$_2$, $C_{1-4}$ alkylamino, and ($C_{1-4}$ alkyl)$_2$-amino;

R$^9$ is independently selected at each occurrence from the group H, $C_{1-4}$ alkyl and $C_{3-8}$ cycloalkyl;

R$^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

R$^{13a}$ and R$^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

R$^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)—, and heteroaryl($C_{1-2}$ alkyl)—;

R$^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

R$^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

R$^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

R$^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

R$^{17}$, R$^{18}$ and R$^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an NR$^{17}$R$^{19}$ moiety, R$^{17}$ and R$^{19}$ taken together form 1-pyrrolidinyl, 1-morpholinyl, 1-piperidinyl or 1-piperazinyl, wherein N$_4$ in 1-piperazinyl is substituted with 0–1 substituents selected from the group R$^{13}$, CO$_2$R$^{14}$, COR$^{14}$ and SO$_2$R$^{14}$;

R$^{17a}$ and R$^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —OR$^{17}$, Br, Cl, F, $C_{1-4}$ haloalkyl, —CN, —S(O)$_n$R$^{18}$, —COR$^{17}$, —CO$_2$R$^{17}$, —NR$^{15}$COR$^{17}$, —NR$^{15}$CO$_2$R$^{18}$, —NR$^{17}$R$^{19}$, and —CONR$^{17}$R$^{19}$; and, heteroaryl is independently selected at each occurence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —OR$^{17}$, —S(O)$_m$R$^{18}$, —COR$^{17}$, —CO$_2$R$^{17}$, —OC(O)R$^{18}$, —NR$^{15}$COR$^{17}$, —N(COR$^{17}$)$_2$, —NR$^{15}$CO$_2$R$^{18}$, —NR$^{17}$R$^{19}$, and —CONR$^{17}$R$^{19}$ and each heteroaryl being substituted on any nitrogen atom with 0–1 substituents selected from the group R CO$_2$R$^{14a}$, COR$^{14a}$ and SO$_2$R$^{14a}$.

[2b] In an even more preferred embodiment, the present invention provides a novel compound of formula I, wherein:

X is selected from the group O, S and a bond

R$^1$ is selected from $C_{1-6}$ alkyl, $C_{3-8}$ cycloalkyl and $C_{3-8}$ cycloalkyl-$C_{1-6}$ alkyl;

R$^1$ is substituted with 0–1 substituents selected from the group —CN, —CO$_2$R$^{13a}$, and $C_{3-8}$ cycloalkyl, wherein 0–1 carbon atoms in the $C_{4-8}$ cycloalkyl is replaced by a group selected from the group —O—, —S(O)$_n$—, and —NR$^{13a}$—; R$^1$ is also substituted with 0–2 substituents independently selected at each occurrence from the group R$^{1a}$, R$^{1b}$, $C_{1-6}$ alkyl, $C_{2-8}$ alkenyl, $C_{2-8}$ alkynyl, Br, Cl, F, CF$_3$, —OR$^{13a}$, —NR$^{13a}$R$^{16a}$, $C_{1-2}$ alkoxy-$C_{1-2}$-alkyl, and $C_{3-6}$ cycloalkyl which is substituted with 0–1 CH$_3$ and in which 0–1 carbons of $C_{4-8}$ cycloalkyl is replaced by —O—;

provided that R$^1$ is other than a cyclohexyl—(CH$_2$)$_2$— group;

R$^{1a}$ is aryl and is phenyl substituted with 0–1 substituents selected from OCH$_3$, OCH$_2$CH$_3$, OCH(CH$_3$)$_2$, OCH$_2$CH$_2$CH$_3$, and OCF$_3$, and 0–3 substituents independently selected at each occurrence from the group CH$_3$, CH$_2$CH$_3$, CH(CH$_3$)$_2$, CH$_2$CH$_2$CH$_3$, cyclopropyl, Br, Cl, F, CF$_3$, —CN, SCH$_3$, —NH$_2$, —NHCH$_3$, —N(CH$_3$)$_2$, —C(O)NH$_2$, —C(O)NHCH$_3$, and —C(O)N(CH$_3$)$_2$;

R$^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group CH$_3$, CH$_2$CH$_3$, CH(CH$_3$)$_2$, CH$_2$CH$_2$CH$_3$, cyclopropyl, OCH$_3$, OCH$_2$CH$_3$, OCH (CH$_3$)$_2$, OCH$_2$CH$_2$CH$_3$, OCF$_3$, Br, Cl, F, CF$_3$, —CN, SCH$_3$, —NH$_2$, —NHCH$_3$, —N(CH$_3$)$_2$, —C(O)NH$_2$, —C(O)NHCH$_3$, and —C(O)N(CH$_3$)$_2$ and each heteroaryl being substituted on any nitrogen atom with 0–1 substituents selected from the group CH$_3$, CO$_2$CH$_3$, COCH$_3$ and SO$_2$CH$_3$;

provided that R$^1$ is other than a —(CH$_2$)$_{1-4}$-aryl or —(CH$_2$)$_{1-4}$-heteroaryl wherein the aryl or heteroaryl group is substituted or unsubstituted;

$R^2$ is selected from the group $CH_3$, $CH_2CH_3$, $CH(CH_3)_2$, and $CH_2CH_2CH_3$;

$R^3$ and $R^8$ are independently selected at each occurrence from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[2c] In a still more preferred embodiment, the present invention provides a novel compound of formula I, wherein:

$R^1$ is substituted $C_1$;

$R^1$ is substituted with 0–1 substituents selected from the group —CN, —$CO_2CH_3$, and —$CO_2CH_2CH_3$;

$R^1$ is also substituted with 0–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH=CH, —CH=$C(CH_3)$, —$CH_2OCH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2OH_3$, and $CH(CH_3)_2$;

$R^3$, $R^7$ and $R^8$ are independently selected at each occurrence from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[2d] In a further preferred embodiment, the present invention provides a novel compound of formula I, wherein:

$R^1$ is substituted (cyclopropyl)-$C_1$ alkyl or (cyclobutyl)-$C_1$ alkyl;

$R^1$ is substituted with 0–1 —CN;

$R^1$ is also substituted with 0–1 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH=CH, —CH=$C(CH_3)$, —$CH_2OCH_3$, —$CH_2CH_2OCH_3$, F, $CF_3$, cyclopropyl, and $CH_3$-cyclopropyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[2e] In another further preferred embodiment, the present invention provides a novel compound of formula I, wherein:

$R^1$ is (cyclopropyl)$C_1$ alkyl or (cyclobutyl)-$C_1$ alkyl substituted with 1 substituent independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=$CH(CH_3)$, —CH=CH, —CH=$C(CH_3)$, —$CH_2OCH_3$, —$CH_2CH_2OCH_3$, F, $CF_3$, cyclopropyl, and $CH_3$-cyclopropyl;

$R^{1a}$ is phenyl substituted with 0–2 substituents independently selected at each occurrence from the group $CH_3$, $CH_2CH_3$, Cl, F, and $CF_3$;

$R^{1b}$ is heteroaryl and is selected from the group furanyl, thienyl, and isoxazolyl, each heteroaryl being substituted on 0–2 carbon atoms with a substituent independently selected at each occurrence from the group $CH_3$, $OCH_3$, Cl, F, and $CF_3$.

[2f] In an even further preferred embodiment, the present invention provides a novel compound of formula I, wherein:

$R^1$ is selected from the group (cyclopropyl)CH—$CH_3$, (cyclopropyl)CH—$CH_2CH_3$, (cyclopropyl)CH—$CH_2OCH_3$, (cyclopropyl) CH—$CH_2CH_2CH_3$, (cyclopropyl) CH—$CH_2CH_2OCH_3$, (cyclopropyl)$_2$CH, phenyl(cyclopropyl)CH, furanyl(cyclopropyl)CH, thienyl(cyclopropyl)CH, isoxazolyl(cyclopropyl)CH, ($CH_3$-furanyl)(cyclopropyl)CH, (cyclobutyl)CH—$CH_3$, (cyclobutyl)CH—$CH_2CH_3$, (cyclobutyl)CH—$CH_2OCH_3$, (cyclobutyl)CH—$CH_2CH_2CH_3$, (cyclobutyl)CH—$CH_2CH_2OCH_3$, (cyclobutyl)$_2$CH, phenyl(cyclobutyl)CH, furanyl(cyclobutyl)CH, thienyl(cyclobutyl)CH, isoxazolyl(cyclobutyl)CH, and ($CH_3$-furanyl)(cyclobutyl)CH;

[2g] In another further preferred embodiment, the present invention provides a novel compound of formula I, wherein:
D is phenyl substituted with 3–5 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[2h] In another further preferred embodiment, the present invention provides a novel compound of formula I, wherein:
D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[2i] In another preferred embodiment, $R^1$ is other than a cyclohexyl-$(CH_2)_{1, 2, 3, 4, 5, 6, 7, 8, 9, \text{or } 10}$-group;

[2j] In another preferred embodiment, $R^1$ is other than an aryl-$(CH_2)_{1, 2, 3, 4, 5, 6, 7, 8, 9, \text{or } 10}$-group, wherein the aryl group is substituted or unsubstituted;

[2k] In another preferred embodiment, $R^1$ is other than a heteroaryl-$(CH_2)_{1, 2, 3, 4, 5, 6, 7, 8, 9, \text{or } 10}$-group, wherein the heteroaryl group is substituted or unsubstituted;

[2l] In another preferred embodiment, $R^1$ is other than a heterocyclyl-$(CH_2)_{1, 2, 3, 4, 5, 6, 7, 8, 9, \text{or } 10}$-group, wherein the heterocyclyl group is substituted or unsubstituted.

[2m] In another preferred embodiment, when D is imidazole or triazole, $R^1$ is other than unsubstituted $C_{1, 2, 3, 4, 5, 6, 7, 8, 9, \text{or } 10}$ linear or branched alkyl or $C_{3, 4, 5, 6, 7, \text{or } 8}$ cycloalkyl.

[2n] In another preferred embodiment, $R^{1a}$ is not substituted with $OR^{17}$.

[2o] In another preferred embodiment, the present invention provides a novel compound of formula I, wherein the compound is selected from:
1-(1-ethyl)propyl-2-ethyl-4-(2,4,5-trichlorophenyl)-1H-benzimidazole,
1-(1-ethyl)propyl-2-methoxy-4-(2,4,5-trichlorophenyl)-1H-benzimidazole,
1-(1-methyl)butyl-2-ethyl-4-(2,4,5-trichlorophenyl)-7-methyl-1H-benzimidazole,
1-(1-methyl)butyl-2-methyl-4-(2,4,5-trichlorophenyl)-1H-benzimidazole,
1-(1-methyl)butyl-2-methoxy-4-(2,4,5-trichlorophenyl)-1H-benzimidazole,
1-(1-butyl)-2-ethyl-4-(2,4,5-trichlorophenyl)-1H-benzimidazole,
1-(1-carbmethoxy)propyl-2-ethyl-4-(2,4,5-trichlorophenyl)-1H-benzimidazole,
1-(1-carbmethoxy)ethyl-2-ethyl-4-(2,4,5-trichlorophenyl)-1H-benzimidazole,
1-(1,1-Dicyclopropyl)methyl-2-ethyl-4-(2,4,5-trichlorophenyl)-1H-benzimidazole,
1-(1,1-Dicyclopropyl)methyl-2-methoxy-4-(2,4,5-trichlorophenyl)-1H-benzimidazole,
1-(1-cyclopropyl)propyl-2-ethyl-4-(2,4,5-trichlorophenyl)-1H-benzimidazole,
1-cyclopentyl-2-ethyl-4-(2,4,5-trichlorophenyl)-1H-benzimidazole,
1-cyclopentyl-2-ethyl-4-(2,4,5-trichlorophenyl)-6-methyl-1H-benzimidazole,
1-(1-phenyl)propyl-2-ethyl-4-(2,4,5-trichlorophenyl)-1H-benzimidazole,
1-(1,1-diphenyl)methyl-2-ethyl-4-(2,4,5-trichlorophenyl)-1H-benzimidazole,
1-cyclopentyl-2-ethyl-4-(2,4,6-trimethylphenyl)benzimidazole,
1-(2-methyl)cyclopentyl-2-ethyl-4-(2,4,6-trimethylphenyl)-1H-benzimidazole,
1-(1,1-dicyclopropyl)methyl-2-ethyl-4-(2,4,6-trichlorophenyl)-1H-benzimidazole,
1-(1,1-dicyclopropyl)methyl-2-ethyl-4-(2,4-dichlorophenyl)-1H-benzimidazole,
1-(1,1-dicyclopropyl)methyl-2-ethyl-4-(2-methyl-4-methoxyphenyl)-1H-benzimidazole,
1-(1-cyclopropyl)butyl-2-ethyl-4-(2-methyl-4-methoxyphenyl)-1H-benzimidazole,
1-(3-pentyl)-2-ethyl-4-(2,4-dimethyl-5-fluorophenyl)-1H-benzimidazole,
1-(2-pentyl)-2-ethyl-4-(2,4-dimethyl-5-fluorophenyl)-1H-benzimidazole,
1-(2-methyl)butyl-2-ethyl-4-(2,4-dichloro-5-fluorophenyl)-1H-benzimidazole,
1-cyclopentyl-2-ethyl-4-(2,4,6-trimethyl-3-pyridyl)-1H-benzimidazole, In another embodiment, the present invention provides pharmaceutical compositions comprising a pharmaceutically acceptable carrier and a therapeutically effective amount of at least one of the compounds of the present invention or a pharmaceutically acceptable salt form thereof.

In another embodiment, the present invention provides a method of treating psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in a mammal, comprising: administering to the mammal a therapeutically effective amount of a compound of formula (I) or a pharmaceutically acceptable salt form thereof.

In another embodiment, the present invention provides intermediate compounds useful in preparation of the CRF antagonist compounds and processes for making those intermediates, as described in the following description and claims.

The CRF antagonist compounds provided by this invention and labelled derivatives thereof are also useful as standards and reagents in determining the ability of a potential pharmaceutical to bind to the CRF receptor.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl. "Halo" or "halogen" as used herein refers to fluoro, chloro, bromo, and iodo; and "counter-ion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and Spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

Combinations of substituents and/or variables are permissible only if such combinations result in stable compounds. A stable compound or stable structure is meant to imply a compound that is sufficiently robust to survive isolation to a useful degree of purity from a reaction mixture, and formulation into an effective therapeutic agent.

The term "therapeutically effective amount" of a compound of this invention means an amount effective to antagonize abnormal level of CRF or treat the symptoms of affective disorder, anxiety or depression in a host.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel benzimidazoles of Formulae (I) of this invention may be prepared by one of the general schemes outlined below (Schemes 1–2). Compounds of Formulae (I) of this invention may be prepared as shown in Scheme I. An appropriately substituted 2-nitroaniline (II) is temporarily protected as the acetamide affording compounds of formula (III). The acetate is shown as example and is not intended to limit the choice of protecting groups at this position. The acetamide formation is typically conducted in the presence of acetic anhydride, although acetyl chloride may also be utilized. The reaction may be conducted in a wide array of typically utilized organic solvents, however, methylene chloride is generally preferred. Subsequent nitration, most commonly with chilled fuming nitric acid, affords in excellent yield the dinitro acetamide (IV). Details for this transformation may be found in the classical teachings of Vivian, etal. (*J. Org. Chem.* 1950, 20, 797).

Formation of compounds of formula (V) proceeds by hydrolysis of the acetamido group (see Green, T. W., Protective Groups in *Organic Synthesis*, John Wiley and Sons, Inc., New York, N.Y., 1991, p.351) and functional group interconversion of the amine to the bromide via either a Sandmeyer reaction or Gatterman reaction via the intermediacy of the corresponding diazonium ion. One familiar in the art of organic synthesis will readily understand the optimal conditions necessary to effect this transformation, and may consult the text of March, J. (*Advanced Organic Chemistry*, John Wiley and Sons, Inc., New York, N.Y., 1985, p.570 and p.647).

Compounds of formula (V) are reduced to the diamines of formula (VI) under a wide variety of potentially optimal conditions known to those skilled in the art. One may also consult the guide of Larock, R. C. (*Comprehensive Organic Transformations: A Guide to Functional Group Preparations*, VCH Publishers, Inc., New York, N.Y., 1989, p.411). The cyclized compounds of formula (VII) may be synthesized by treatment of diamines of formula (VI) with an ortho acid derivative of the formula (alkyl—O)$_3$C—X—R$^2$ where alkyl is preferably methyl, ethyl or propyl. The cyclizations are preferably carried out in the presence of an acid catalyst such as, but not limited to, hydrochloric acid, hydrobromic acid, nitric acid or an organic acid such as, but not limited to, propionic acid. The reactions are conducted at room temperature or optionally at elevated temperature up to boiling to effect loss of (alkyl—OH) from the reaction.

Treatment of compounds of formula (VII) with a base and a compound of formula R$^1$-X wherein X represents a leaving group may afford the desired benzimidazole compounds of formula (VIII). Leaving groups may include, but are not limited to, bromo, chloro, iodo, cyano, alkoxy, methanesulfonyl, and p-toluenesulfonyl. Possible bases include, but are not limited to, the sodium, lithium or potassium bis(trimethylsilyl)amides, sodium or potassium hydride, alkyl lithiums and alkyl grignards and inorganic bases such as sodium, potassium and lithium hydroxide. The reactions are optionally conducted at room temperature or at elevated temperatures up to the boiling point of a cosolvent.

A wide variety of inert solvents may be employed, for example, dimethylformamide, dimethylsulfoxide, toluene, tetrahydrofuran, diethyl ether, and methylene chloride. The reactions may be successfully performed in glass reaction vessels or polypropylene wells, and one skilled in the art of organic chemistry will readily understand the optimal combinations of above conditions for effecting this transformation. Although regiomeric alkylation products are conceivable from tautomers of formula (VII), the experimental conditions taught herein will selectively provide the desired regiomer represented by compounds of formula (VIII). Alternatively, compounds of formula (VIII) may be formed under the classic conditions of the Mitsunobu reaction (Synthesis, 1980, p.1) from compounds of formula (VII) and an alcohol $R^1$—OH.

Finally, the benzimidazoles of formula (I) may be formed from precursors of formula (VIII) by treatment with boronic acids of formula D-B(OH)$_2$ in the necessary presence of a palladium source, noteably Pd(OAc)$_2$ with the additives triphenyl-phosphine and sodium carbonate. The preferred solvent of the Suzuki coupling is dimethoxyethane, although other inert organic solvents such as diethyl ether, and tetrahydrofuran may also be employed. The reaction is effected at room temperature or at temperatures up to the boiling point of the solvent. One skilled in the art will understand optimized conditions as taught by Larsen, R. D. (*J. Org. Chem.* 1994, 54, 6391–6394).

Alternatively, the benzimidazoles of formula (I) may also be prepared according to Scheme 2. A similiar teaching also appears in EP 0812831 (vide supra). Thus, under conditions taught in Scheme 1, the aryl bromides of formula (IX) are coupled to reagents of formula D-B(OH)$_2$ to afford compounds of formula (X). For the preparation of compounds of formula (IX), one may refer to the art of Peet, etal. (*J. Heterocyclic Chem.* 1979, 16, 33–39) for details ($R^3$=$R^7$=$R^8$=H). Hydrolysis of the carboalkoxy of compounds of formula (X) under conditions familiar to anyone in the art affords the acid derivatives of formula (XI) which are then subjected to a modified Curtius rearrangement (see March, J., *Advanced Organic Chemistry*, John Wiley and Sons, Inc., New York, N.Y., 1985, p.984) in the presence of diphenylphosphoryl azide and a trialkyl amine base in an inert solvent (ie. dry benzene, dry toluene). The reaction is preferably refluxed for one hour, cooled and treated with t-butanol and heated for an additional 2–24 hours to effect incorporation of the t-butyl carbamate, providing compounds of formula (XII, PG=Boc).

Reduction of compounds of formula (XII) under a wide variety of methods known to those skilled in the art affords cleanly the aryl diamines of formula (XIII). Common reduction methods include hydrogenation in the presence of a catalyst such as Raney nickel (RaNi) or palladium on carbon (Pd/C) in an inert alcohol solvent (methanol, ethanol) or ethyl acetate. The reactions are optionally run under pressure and at elevated temperature (60° C.). Alternatively, and preferably, the reduction may be effected in exceptionally high yield by treatment of compounds of formula (XII) with sodium dithionite in the presence of ammonium hydroxide. One optimal solvent combination for this reduction is a mixture of dioxane/water (1:1).

Formation of compounds of formula (XIV) is achieved by a common reductive amination procedure employing compounds of formula (XIII) and the appropriate $R^1$ aldehydes and ketones. The reaction is preferably conducted under anhydrous conditions in the presence of a dehydrating agent (ie, sodium sulfate, magnesium sulfate) and acid catalyst (ie. hydrochloric acid, sulfuric acid, or acetic acid). Examples of suitable reducing agents which are intended to exemplify and not limit the invention are sodium triacetoxyborohydride and sodium cyanoborohydride. Compounds of formula (XIV) are then deprotected under common conditions (PG=Boc, see, Green, T. W. *Protective Groups in Organic Synthesis*, John Wiley and Sons, Inc., New York, N.Y., 1991, p.328) to afford pre-cyclization compounds of formula (XV).

Finally, the desired benzimidazoles of formula (I) are readily afforded from compounds of formula (XV) as described in Scheme 1 for the formation of (I) from compounds of formula (VIII).

SCHEME 1

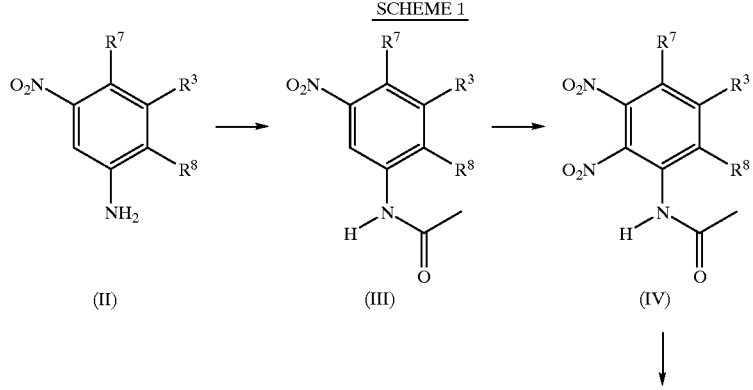

-continued
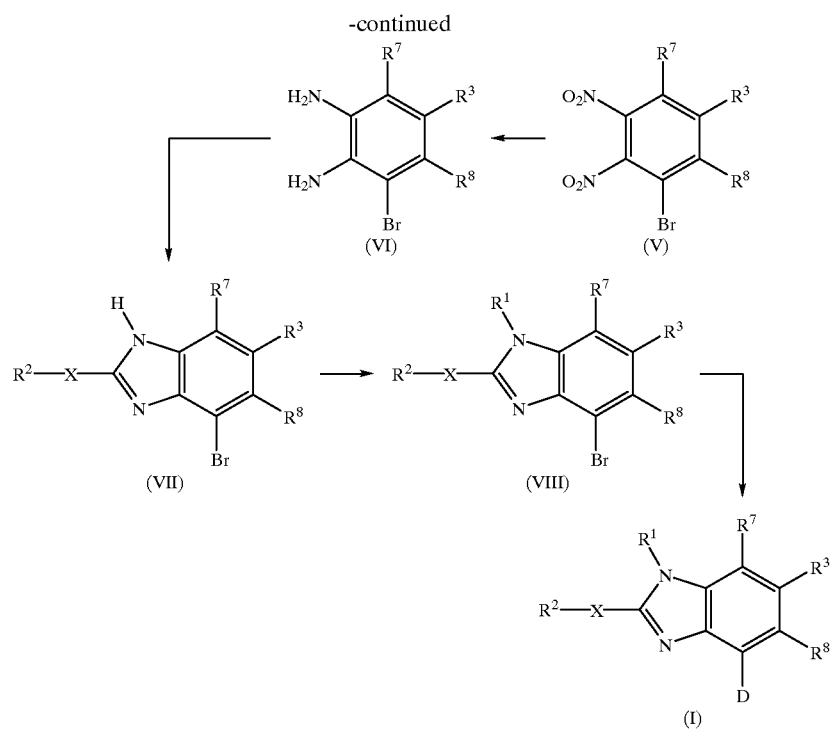
SCHEME 2
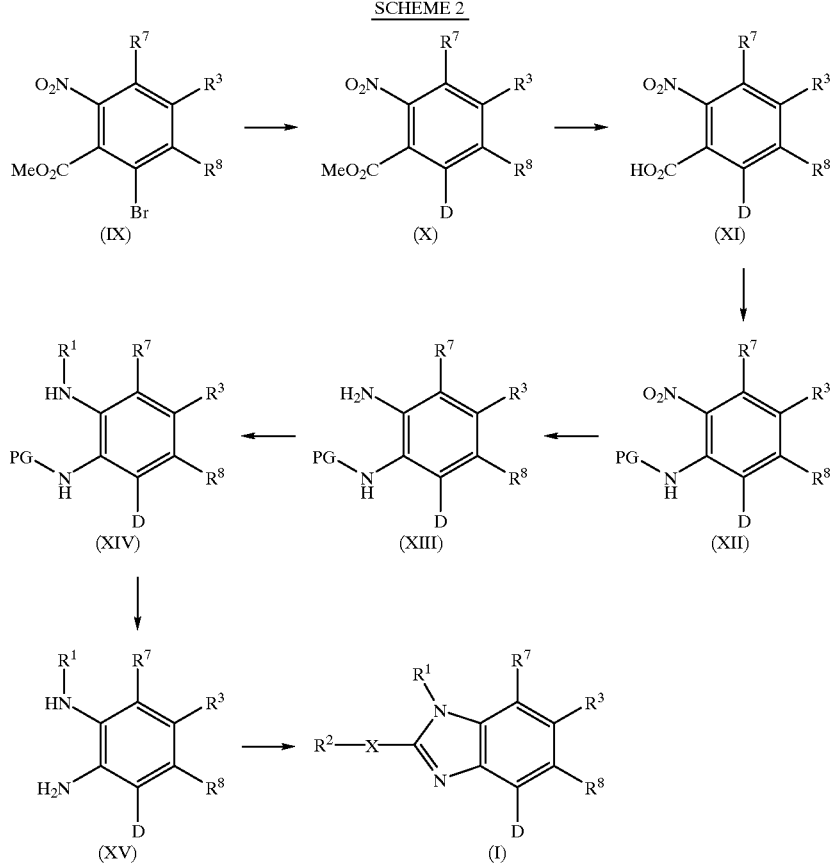

The following example is provided to describe the invention in further detail. The example, which sets forth the best mode presently contemplated for carrying out the invention, is intended to illustrate and not to limit the invention.

EXAMPLE 1

2-Ethyl-1-(1-ethyl-propyl)-4-(2,4,5-trichloro-phenyl)-1H-benzimidazole

Step A:
2'; 4', 5'-Trichloro-3-nitro-biphenyl-2-carboxylic acid methyl ester

Under a nitrogen atmosphere in 15 ml of anhydrous dimethoxyethane (DME) was dissolved 461 mg (1.76 mmol) triphenylphosphine. The reaction was evacuated and repressurized under nitrogen and stirred for 15 minutes at which point 98.55 mg of palladium acetate was added. The reaction was stirred for an additional 15 minutes at which point 1.10 g (4.88 mmol) of 2,4,5-trichlorophenylboronic acid was added. The reaction was stirred another 15 minutes at which time 1.14 g (4.39 mmol) of methyl 2-bromo-5-nitrobenzoate and 5 ml of 2N sodium carbonate were added. The reaction was evacuated and repressurized under nitrogen and heated to reflux for 18 hours at which time it was cooled, poured into 250 ml water, and extracted with ethyl acetate (3×50 ml). The combined organic extracts were dried over magnesium sulfate, filtered and evaporated in vacuo to afford the crude product as a brown oil. The crude product was purified by column chromatography on silica gel (275 g) and eluted with 20% ethyl acetate in hexanes to afford 740 mg (47%) of the title compound.

$^1$H NMR (CDCl$_3$) 8.22 (dd, 1H, J=7 Hz, 1 Hz), 7.61 (m, 3H), 7.41 (s, 1H), 3.74 (s, 3H).

Step B:
2', 4', 5'-Trichloro-3-nitro-biphenyl-2-carboxylic acid

Under a nitrogen atmosphere was combined 735 mg (2.03 mmol) of the title compound Step A, 5 ml of tetrahydrofuran (THF), 3 ml of methanol, and 5 ml of water. To this solution was added 320 mg (8 mmol) of freshly powdered sodium hydroxide and the resulting solution was heated to reflux for 90 minutes. The reaction was cooled and concentrated in vacuo, diluted with 40 ml water and extracted with ethyl acetate (1×25 ml). After separation the aqueous layer was acidified to pH <2 with 6.25N hydrochloric acid (HCl) and extracted with ethyl acetate (3×25 ml). The combined organic extracts from the acidified water layer were dried over magnesium sulfate, filtered, and concentrated in vacuo to yield 700 mg (100%) of the title compound.

$^1$H NMR (CDCl$_3$) 8.23 (dd, 1H, J=7 Hz, 1 Hz), 7.61 (m, 3H), 7.26 (s, 1H). HRMS (M−H)$^-$ calcd for C$_{16}$H$_5$Cl$_3$N$_1$O 343.9284, found 343.9297.

Step C:
(2', 4', 5'-Trichloro-3-nitro-biphenyl-2-yl)-carbamic acid tert-butyl ester Under a nitrogen atmosphere in 20 ml of anhydrous benzene was combined 700 mg (2.03 mmol) of the title compound in Step B and 2.03 ml of triethylamine (TEA). To this solution was added 437 ml (2.03 mmol) of diphenylphosphoryl azide, and the resulting solution was heated to reflux for 1 hour. After completion the reaction mixture was cooled and 301 mg (4.06 mmol) of t-butanol was added, and the solution was heated to reflux for an additional 16 hours. The reaction mixture was concentrated in vacuo and purified by column chromatography on silica gel (200 g) and eluted using 20% ethyl acetate in hexanes to afford 502 mg (59%) of the title compound as a light yellow solid.

$^1$H NMR (CDCl$_3$) 8.06 (dd, 1H, J=7 Hz, 1.5 Hz), 7.62 (s, 1H), 7.49 (m, 3H), 1.28 (s, 9H). HRMS (M−H)$^-$ calcd for C$_{17}$H$_{14}$Cl$_3$N$_2$O 415.0019, found 415.0014.

Step D:
(3-Amino-2',4',5'-trichloro-biphenyl-2-yl)-carbamic acid tert-butyl ester To 12 ml of a 1:1 solution of dioxane and water was added 500 mg (1.2 mmol) of the title compound in Step C and 0.6 ml of concentrated ammonium hydroxide. To this suspension was added 1.67 g (9.6 mmol) of sodium dithionite. The reaction mixture was stirred at room temperature for 2.5 hours and then concentrated in vacuo. The resulting oil was dissolved in 1:1 ethyl acetate and water and the layers separated. The aqueous layer was extracted with ethyl acetate (2×25 ml) and the combined organic extracts dried over magnesium sulfate, filtered, and evaporated to yield 536.6 mg (100%) of the title compound as a beige solid. 1H NMR (DMSO d$_6$) 8.00 (br s, 1H), 7.80 (s, 1H), 7.40 (s, 1H), 6.98 (t, 1H, J=8 Hz), 6.74 (d, 1H, i=7.5 Hz), 6.43 (d, 1H, J=7 Hz), 1.16 (br s, 9H). HRMS (M+H)$^+$ calcd for C$_{17}$H18Cl$_3$N$_2$O$_2$ 387.0433, found 387.0421.

Step E:
[3(1-Ethyl-propylamino)-2',4',5'-trichloro-binhenyl-2-yl]-carbamic acid tert-butyl ester Under a nitrogen atmosphere was combined 5 ml of acetic acid, 232 mg (0.6 mmol) of the title compound in Step D and 122 ml of 3-pentanone. To this solution was added 853 mg (6 mmol) of sodium sulfate. The solution was stirred at room temperature for 25 minutes at which time 153 mg (0.72 mmol) of sodiumtriacetoxyborohydride was added. The reaction was allowed to stir at room temperature for an additional 1 hour and then quenched with aqueous sodium carbonate (100 ml) and extracted with ethyl acetate (3×20 ml). The combined organic extracts were dried over sodium sulfate, filtered, and evaporated to afford the crude product as a light brown oil. The crude product was purified by column chromatography on silica gel (30 g) and eluted with 20% ethyl acetate in hexanes to afford 171 mg (62%) of the title compound.

$^1$H NMR (CDCl$_3$) 7.55 (s, 1H), 7,41 (br s, 1H), 7.21 (t, 1H, J=8 Hz), 6.71 (d, 1H, J=8 Hz), 6.46 (d, 1H, J=7 Hz), 3.32 (m, 1H), 1.58 (m, 4H), 1.3 (S, 9H), 0.9 (m, 6H). HRMS (M+H)$^+$ calcd for C$_{22}$H$_{28}$Cl$_3$N$_2$O$_2$ 457.1216, found 457.1211.

Step F:
N-3-(1-Ethyl-propylamino)-2',4',5'-trichloro-biphenyl-2,3-diamine

Under a nitrogen atmosphere was dissolved 171 mg (0.37 mmol) of the title compound in Step E in 1 ml of dichloromethane and the resulting solution chilled to 0° C. Trifluoroacetic acid (12 ml) was added dropwise over 4 minutes and the reaction stirred at 0° C. for 1 hour and then allowed to warm to room temperature and stir for an additional 1 hour. Reaction was then evaporated in vacuo and the residual oil taken up in dichloromethane. The organic layer was washed with 1N sodium hydroxide (1×25 ml) and the layers separated. The aqueous layer was extracted with dichloromethane (2×25 ml) and the combined organic extracts dried over sodium sulfate filtered and evaporated to yield 129 mg (99%) of the product as a brown oil.

1H NMR (CDCl$_3$) 7.62 (S, 1H), 7.46 (S, 1H), 6.86 (t, 1H, J=8 Hz), 6.69 (d, 1H, J=7 Hz), 6.48 (d, 1H, J=6 Hz), 3.25 (m, 1H), 1.60 (m, 4H), 0.95 (m, 6H). HRMS (M+H)$^+$ calcd for C$_{17}$H$_{20}$Cl$_3$N$_2$ 357.0692, found 357.0693.

Step G:
2-Ethyl-1-(1-ethyl-propyl)-4-(2,4,5-trichloro-phenyl)-1H-benzimidazole

Under a nitrogen atmosphere was combined 129 mg (0.36 mmol) of the title compound of Step F in 5 ml of triethylorthopropionate. To the resulting solution was added 2 drops of concentrated hydrochloric acid. The reaction was allowed to stir at room temperature for 8 hours and then poured into 100 ml of water. The reaction was extracted with ethyl acetate (4×20 ml) and the combined organic extracts dried over sodium sulfate, filtered, and evaporated to yield the crude product as a light brown crystal. The crude product was purified by column chromatography on silica gel (20 g) and eluted with 20% ethyl acetate in hexanes to yield 101 mg (71%) of the title compound as a brown solid. M.P. =150.0–151.5° C.; 1H NMR (CDCl$_3$) 7.72 (s, 1H), 7.61 (s, 1H), 7.52 (m, 1H), 7.20 (m, 2H), 4.10 (m, 1H), 2.92 (q, 2H, J=8 Hz), 2.18 (m, 2H), 2.05 (m, 2H), 1.38 (t, 3H, J=8 Hz), 0.83 (t, 6H, J=7.5 Hz); HRMS calc. for $C_{20}$ $H_{21}$ $N_2$ $Cl_3$: (M+H)$^+$ 395.0849, Found 395.0846; Anal Calcd for $C_{20}$ $H_{21}$ $N_2$ $Cl_3$: C, 60.70; H, 5.358; N, 7.088. Found C, 60.40; H, 5.46; N, 6.75.

The foregoing tables contain further examples which are meant to be illustrative of the present invention, and not to be taken as limiting thereof.

TABLE 1

| Ex. | $R^1$ | X | $R^2$ | $R^3$ | $R^7$ | $R^8$ | Mass Spec |
|---|---|---|---|---|---|---|---|
| 1 | CH(CH$_2$CH$_3$)$_2$ | CH$_2$ | CH$_3$ | H | H | H | 395.09 |
| 2 | CH(CH$_2$CH$_3$)$_2$ | CH$_2$ | CH$_3$ | CH$_3$ | H | H | |
| 3 | CH(CH$_2$CH$_3$)$_2$ | CH$_2$ | CH$_3$ | H | CH$_3$ | H | |
| 4 | CH(CH$_2$CH$_3$)$_2$ | CH$_2$ | H | H | H | H | |
| 5 | CH(CH$_2$CH$_3$)$_2$ | O | CH$_3$ | H | H | H | |
| 6 | CH(CH$_2$CH$_3$)$_2$ | O | CH$_3$ | H | H | CH$_3$ | |
| 7 | CH(CH$_2$CH$_3$)$_2$ | CH$_2$ | CH$_2$CH$_3$ | H | H | H | |
| 8 | CH(CH$_3$)CH$_2$CH$_2$CH$_3$ | CH$_2$ | CH$_3$ | H | CH$_3$ | H | |
| 9 | CH(CH$_3$)CH$_2$CH$_2$CH$_3$ | CH$_2$ | H | H | H | H | |
| 10 | CH(CH$_3$)CH$_2$CH$_2$CH$_3$ | O | CH$_3$ | H | H | H | |
| 11 | CH(CH$_3$)CH$_2$CH$_2$CH$_3$ | O | CH$_3$ | H | H | CH$_3$ | |
| 12 | CH$_2$CH$_2$CH$_3$ | CH$_2$ | CH$_3$ | H | H | H | |
| 13 | CH$_2$CH$_2$CH$_2$CH$_3$ | CH$_2$ | CH$_3$ | H | H | H | |
| 14 | CH$_2$CH(CH$_2$CH$_3$)$_2$ | CH$_2$ | CH$_3$ | H | H | H | |
| 15 | CH$_2$CH$_2$CH(CH$_3$)$_2$ | CH$_2$ | CH$_3$ | H | H | H | |
| 16 | CH(CO$_2$CH$_3$)CH$_2$CH$_3$ | CH$_2$ | CH$_3$ | H | H | H | |
| 17 | CH(CO$_2$CH$_2$CH$_3$)CH$_3$ | CH$_2$ | CH$_3$ | H | H | H | |
| 18 | CH(COCH$_3$)CH$_2$CH$_3$ | CH$_2$ | CH$_3$ | H | H | H | |
| 19 | CH(COPh)CH$_2$CH$_3$ | CH$_2$ | CH$_3$ | H | H | H | |
| 20 | CH$_2$CH$_2$C≡CCH$_3$ | CH$_2$ | CH$_3$ | H | H | H | |
| 21 | CH(cyclo-Pr)$_2$ | CH$_2$ | CH$_3$ | H | H | H | |
| 22 | CH(cyclo-Pr)$_2$ | CH$_2$ | CH$_3$ | CH$_3$ | H | H | |
| 23 | CH(cyclo-Pr)$_2$ | CH$_2$ | CH$_3$ | H | CH$_3$ | H | |
| 24 | CH(cyclo-Pr)$_2$ | CH$_2$ | H | H | H | H | |
| 25 | CH(cyclo-Pr)$_2$ | CH$_2$ | H | H | CH$_3$ | H | |
| 26 | CH(cyclo-Pr)$_2$ | O | CH$_3$ | H | H | CH$_3$ | |
| 27 | CH(cyclo-Pr)$_2$ | O | CH$_3$ | H | H | H | |
| 28 | CH(cyclo-Pr)$_2$ | CH$_2$ | CH$_2$CH$_3$ | H | H | H | |
| 29 | CH$_2$cyclopropyl | CH$_2$ | CH$_3$ | H | H | H | |
| 30 | CH$_2$cyclopropyl | CH$_2$ | CH$_3$ | CH$_3$ | H | H | |
| 31 | CH$_2$cyclopropyl | CH$_2$ | CH$_3$ | H | CH$_3$ | H | |
| 32 | CH(Et)(c-Pr) | CH$_2$ | CH$_3$ | H | H | H | |
| 33 | CH(Et)(c-Pr) | CH$_2$ | CH$_3$ | CH$_3$ | H | H | |
| 34 | CH(Et)(c-Pr) | CH$_2$ | CH$_3$ | H | CH$_3$ | H | |
| 35 | CH(Et)(c-Pr) | CH$_2$ | H | H | H | H | |
| 36 | CH$_2$CH$_2$OCH$_2$CH$_3$ | CH$_2$ | CH$_3$ | H | H | H | |
| 37 | CH$_2$CH$_2$OCH$_2$CH$_3$ | CH$_2$ | H | H | H | H | |
| 38 | CH$_2$CH$_2$OCH$_2$CH$_3$ | O | CH$_3$ | H | H | H | |
| 39 | cyclopentyl | CH$_2$ | CH$_3$ | H | H | H | |
| 40 | cyclopentyl | CH$_2$ | CH$_3$ | Me | H | H | |
| 41 | cyclohexyl | CH$_2$ | CH$_3$ | H | H | H | |
| 42 | cyclohexyl | CH$_2$ | CH$_3$ | H | Me | H | |
| 43 | CH$_2$Ph | CH$_2$ | CH$_3$ | H | H | H | |
| 44 | CH$_2$Ph | O | CH$_3$ | H | H | H | |
| 45 | CH(Ph)CH$_2$CH$_3$ | CH$_2$ | CH$_3$ | H | H | H | |
| 46 | CH(Ph)$_2$ | CH$_2$ | CH$_3$ | H | H | H | |
| 47 | CH$_2$-(2-chloroPh) | CH$_2$ | CH$_3$ | H | H | H | |

TABLE 1-continued

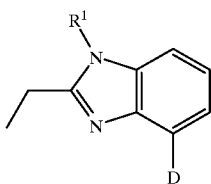

| Ex. | R$^1$ | X | R$^2$ | R$^3$ | R$^7$ | R$^8$ | Mass Spec |
|---|---|---|---|---|---|---|---|
| 48 | CH$_2$-(4-chloroPh) | CH$_2$ | CH$_3$ | H | H | H | |
| 49 | CH$_2$-(4-MeO—Ph) | CH$_2$ | CH$_3$ | H | H | H | |
| 50 | CH$_2$-(4-CF$_3$O—Ph) | CH$_2$ | CH$_3$ | H | H | H | |

TABLE 2

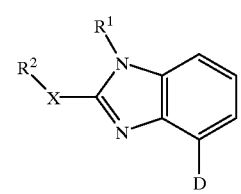

| Ex. | R$^1$ | D |
|---|---|---|
| 1 | cyclopentyl | 2,4,6-trimethylphenyl |
| 2 | cyclohexyl | 2,4,6-trimethylphenyl |
| 3 | 2-methyl(c-pentyl) | 2,4,6-trimethylphenyl |
| 4 | benzyl | 2,4,6-trimethylphenyl |
| 5 | 2-chlorobenzyl | 2,4,6-trimethylphenyl |
| 6 | 4-chlorobenzyl | 2,4,6-trichlorophenyl |
| 7 | CH(cyclopropyl)$_2$ | 2,4,6-trichlorophenyl |
| 8 | 4-fluorobenzyl | 2,4-dichlorophenyl |
| 9 | CH(cyclopropyl)$_2$ | 2-chloro-4-bromophenyl |
| 10 | 4-bromobenzyl | 2-chloro-4-bromophenyl |
| 11 | 4-methoxybenzyl | 2-chloro-4-bromophenyl |
| 12 | CH(cyclopropyl)$_2$ | 2-thiomethyl-4-bromophenyl |
| 13 | CH(cyclopropyl)$_2$ | 2-methyl-4-methoxyphenyl |
| 14 | CH(c-Pr)CH$_2$CH$_2$CH$_3$ | 2-methyl-4-methoxyphenyl |
| 15 | CH$_2$CH$_2$CH$_2$CH$_3$ | 2,4-dimethyl-5-fluorophenyl |
| 16 | CH(CH$_2$CH$_3$)$_2$ | 2,4-dimethyl-5-fluorophenyl |
| 17 | CH(CH$_3$)CH$_2$CH$_2$CH$_3$ | 2,4-dimethyl-5-fluorophenyl |
| 18 | CH$_2$CH(CH$_3$)CH$_2$CH$_3$ | 2,4-dichloro-5-fluorophenyl |
| 19 | CH$_2$CH$_2$OCH$_2$CH$_3$ | 2,4-dichloro-5-fluorophenyl |
| 20 | CH(Ph)(c-Pr) | 2-bromo-4-dimethylaminophenyl |
| 21 | CH(4-F—Ph)(c-Pr) | 2-methyl-4-dimethylaminophenyl |
| 22 | cyclopentyl | 2,4,6-trimethyl-3-pyridyl |
| 23 | cyclohexyl | 2,4,6-trimethyl-3-pyridyl |
| 24 | 2-methyl(c-pentyl) | 2,4,6-trimethyl-3-pyridyl |
| 25 | benzyl | 2,4,6-trimethyl-3-pyridyl |
| 26 | CH(CH$_2$CH$_3$)$_2$ | 2,4,6-trimethyl-3-pyridyl |
| 27 | cyclopentyl | 2,4-dimethyl-3-pyridyl |
| 28 | cyclohexyl | 4,6-dimethyl-3-pyridyl |
| 29 | 2-methyl(c-pentyl) | 2,4-dimethoxy-3-pyridyl |
| 30 | benzyl | 2-methyl-4-dimethylamino-3-pyridyl |
| 31 | 2-methyl(c-pentyl) | 6-methyl-4-dimethylamino-3-pyridyl |
| 32 | benzyl | 2,4,6-trimethyl-3,5-pyrimidyl |
| 33 | CH(CH$_2$CH$_3$)$_2$ | 2,4-dimethyl-3,5-pyrimidyl |
| 34 | cyclopentyl | 4-isopropyl-2-furanyl |
| 35 | cyclohexyl | 5-isopropyl-2-furanyl |
| 36 | 2-methyl(c-pentyl) | 4-isopropyl-2-thiophenyl |
| 37 | benzyl | 5-isopropyl-2-thiophenyl |

TABLE 3

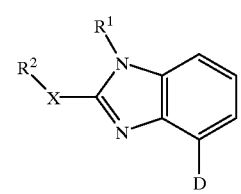

a$_1$ R$^2$X = CH$_3$O
a$_2$ R$^2$X = CH$_3$S
a$_3$ R$^2$X = Me
a$_4$ R$^2$X = Et
a$_5$ R$^2$X = n-Pr

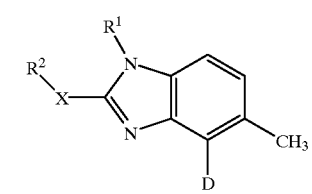

b$_1$ R$^2$X = CH$_3$O
b$_2$ R$^2$X = CH$_3$S
b$_3$ R$^2$X = Me
b$_4$ R$^2$X = Et
b$_5$ R$^2$X = n-Pr

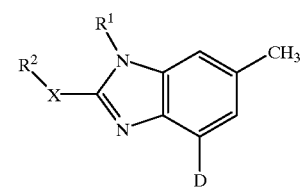

c$_1$ R$^2$X = CH$_3$O
c$_2$ R$^2$X = CH$_3$S
c$_3$ R$^2$X = Me
c$_4$ R$^2$X = Et
c$_5$ R$^2$X = n-Pr

TABLE 3-continued

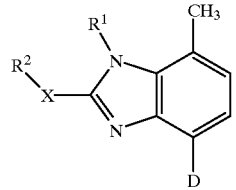

d₁ R²X = CH₃O
d₂ R²X = CH₃S
d₃ R²X = Me
d₄ R²X = Et
d₅ R²X = n-Pr

| Ex. # | R¹ | D |
|---|---|---|
| 1 | (cPr)₂CH | 2-Cl-4-MeO-phenyl |
| 2 | phenyl(cPr)CH | 2-Cl-4-MeO-phenyl |
| 3 | 2-furanyl(cPr)CH | 2-Cl-4-MeO-phenyl |
| 4 | 3-furan(cPr)CH | 2-Cl-4-MeO-phenyl |
| 5 | 2-thienyl(cPr)CH | 2-Cl-4-MeO-phenyl |
| 6 | 3-thienyl(cPr)CH | 2-Cl-4-MeO-phenyl |
| 7 | 2-isoxazolyl(cPr)CH | 2-Cl-4-MeO-phenyl |
| 8 | 2-(5-CH₃-furanyl)(cPr)CH | 2-Cl-4-MeO-phenyl |
| 9 | 2-(4-CH₃-isoxazolyl)(cPr)CH | 2-Cl-4-MeO-phenyl |
| 10 | cPr-CH(CH₃) | 2-Cl-4-MeO-phenyl |
| 11 | 1-cPr-CH(CH₂CH₃) | 2-Cl-4-MeO-phenyl |
| 12 | 1-cPr-CH(CH₂CH₂CH₃) | 2-Cl-4-MeO-phenyl |
| 13 | 1-cPr-CH(CH₂OCH₃) | 2-Cl-4-MeO-phenyl |
| 14 | 1-cPr-CH(CH₂CH₂OCH₃) | 2-Cl-4-MeO-phenyl |
| 15 | (cBu)₂CH | 2-Cl-4-MeO-phenyl |
| 16 | phenyl(cBu)CH | 2-Cl-4-MeO-phenyl |
| 17 | 2-furanyl(cBu)CH | 2-Cl-4-MeO-phenyl |
| 18 | 3-furan(cBu)CH | 2-Cl-4-MeO-phenyl |
| 19 | 2-thienyl(cBu)CH | 2-Cl-4-MeO-phenyl |
| 20 | 3-thienyl(cBu)CH | 2-Cl-4-MeO-phenyl |
| 21 | 2-isoxazolyl(cBu)CH | 2-Cl-4-MeO-phenyl |
| 22 | 2-(5-CH₃-furanyl)(cBu)CH | 2-Cl-4-MeO-phenyl |
| 23 | 2-(4-CH₃-isoxazolyl)(cBu)CH | 2-Cl-4-MeO-phenyl |
| 24 | cBu-CH(CH₃) | 2-Cl-4-MeO-phenyl |
| 25 | 1-cBu-CH(CH₂CH₃) | 2-Cl-4-MeO-phenyl |
| 26 | 1-cBu-CH(CH₂CH₂CH₃) | 2-Cl-4-MeO-phenyl |
| 27 | 1-cBu-CH(CH₂OCH₃) | 2-Cl-4-MeO-phenyl |
| 28 | 1-cBu-CH (CH₂CH₂OCH₃) | 2-Cl-4-MeO-phenyl |
| 29 | (cPr)₂CH | 2-Cl-4-CF₃-phenyl |
| 30 | phenyl(cPr)CH | 2-Cl-4-CF₃-phenyl |
| 31 | 2-furanyl(cPr)CH | 2-Cl-4-CF₃-phenyl |
| 32 | 3-furan(cPr)CH | 2-Cl-4-CF₃-phenyl |
| 33 | 2-thienyl(cPr)CH | 2-Cl-4-CF₃-phenyl |
| 34 | 3-thienyl(cPr)CH | 2-Cl-4-CF₃-phenyl |
| 35 | 2-isoxazolyl(cPr)CH | 2-Cl-4-CF₃-phenyl |
| 36 | 2-(5-CH₃-furanyl)(cPr)CH | 2-Cl-4-CF₃-phenyl |
| 37 | 2-(4-CH₃-isoxazolyl)(cPr)CH | 2-Cl-4-CF₃-phenyl |
| 38 | cPr-CH(CH₃) | 2-Cl-4-CF₃-phenyl |
| 39 | 1-cPr-CH(CH₂CH₃) | 2-Cl-4-CF₃-phenyl |
| 40 | 1-cPr-CH(CH₂CH₂CH₃) | 2-Cl-4-CF₃-phenyl |
| 41 | 1-cPr-CH(CH₂OCH₃) | 2-Cl-4-CF₃-phenyl |
| 42 | 1-cPr-CH(CH₂CH₂OCH₃) | 2-Cl-4-CF₃-phenyl |
| 43 | (cBu)₂CH | 2-Cl-4-CF₃-phenyl |
| 44 | phenyl(cBu)CH | 2-Cl-4-CF₃-phenyl |
| 45 | 2-furanyl(cBu)CH | 2-Cl-4-CF₃-phenyl |
| 46 | 3-furan(cBu)CH | 2-Cl-4-CF₃-phenyl |
| 47 | 2-thienyl(cBu)CH | 2-Cl-4-CF₃-phenyl |
| 48 | 3-thienyl(cBu)CH | 2-Cl-4-CF₃-phenyl |
| 49 | 2-isoxazolyl(cBu)CH | 2-Cl-4-CF₃-phenyl |
| 50 | 2-(5-CH₃-furanyl)(cBu)CH | 2-Cl-4-CF₃-phenyl |
| 51 | 2-(4-CH₃-isoxazolyl)(cBu)CH | 2-Cl-4-CF₃-phenyl |
| 52 | cBu-CH(CH₃) | 2-Cl-4-CF₃-phenyl |
| 53 | 1-cBu-CH(CH₂CH₃) | 2-Cl-4-CF₃-phenyl |
| 54 | 1-cBu-CH(CH₂CH₂CH₃) | 2-Cl-4-CF₃-phenyl |
| 55 | 1-cBu-CH(CH₂OCH₃) | 2-Cl-4-CF₃-phenyl |
| 56 | 1-cBu-CH(CH₂CH₂OCH₃) | 2-Cl-4-CF₃-phenyl |
| 57 | (cPr)₂CH | 2,4-diCl-phenyl |
| 58 | phenyl(cPr)CH | 2,4-diCl-phenyl |
| 59 | 2-furanyl(cPr)CH | 2,4-diCl-phenyl |
| 60 | 3-furan(cPr)CH | 2,4-diCl-phenyl |
| 61 | 2-thienyl (cPr)CH | 2,4-diCl-phenyl |
| 62 | 3-thienyl(cPr)CH | 2,4-diCl-phenyl |
| 63 | 2-isoxazolyl(cPr)CH | 2,4-diCl-phenyl |
| 64 | 2-(5-CH₃-furanyl)(cPr)CH | 2,4-diCl-phenyl |
| 65 | 2-(4-CH₃-isoxazolyl)(cPr)CH | 2,4-diCl-phenyl |
| 66 | cPr-CH(CH₃) | 2,4-diCl-phenyl |
| 67 | 1-cPr-CH(CH₂CH₃) | 2,4-diCl-phenyl |
| 68 | 1-cPr-CH(CH₂CH₂CH₃) | 2,4-diCl-phenyl |
| 69 | 1-cPr-CH(CH₂OCH₃) | 2,4-diCl-phenyl |
| 70 | 1-cPr-CH(CH₂CH₂OCH₃) | 2,4-diCl-phenyl |
| 71 | (cBu)₂CH | 2,4-diCl-phenyl |
| 72 | phenyl(cBu)CH | 2,4-diCl-phenyl |
| 73 | 2-furanyl(cBu)CH | 2,4-diCl-phenyl |
| 74 | 3-furan(cBu)CH | 2,4-diCl-phenyl |
| 75 | 2-thienyl(cBu)CH | 2,4-diCl-phenyl |
| 76 | 3-thienyl(cBu)CH | 2,4-diCl-phenyl |
| 77 | 2-isoxazolyl(cBu)CH | 2,4-diCl-phenyl |
| 78 | 2-(5-CH₃-furanyl)(cBu)CH | 2,4-diCl-phenyl |
| 79 | 2-(4-CH₃-isoxazolyl)(cBu)CH | 2,4-diCl-phenyl |
| 80 | cBu-CH(CH₃) | 2,4-diCl-phenyl |
| 81 | 1-cBu-CH(CH₂CH₃) | 2,4-diCl-phenyl |
| 82 | 1-cBu-CH(CH₂CH₂CH₃) | 2,4-diCl-phenyl |
| 83 | 1-cBu-CH (CH₂OCH₃) | 2,4-diCl-phenyl |
| 84 | 1-cBu-CH(CH₂CH₂OCH₃) | 2,4-diCl-phenyl |
| 85 | (cPr)₂CH | 2,5-diCl-phenyl |
| 86 | phenyl(cPr)CH | 2,5-diCl-phenyl |
| 87 | 2-furanyl(cPr)CH | 2,5-diCl-phenyl |
| 88 | 3-furan(cPr)CH | 2,5-diCl-phenyl |
| 89 | 2-thienyl(cPr)CH | 2,5-diCl-phenyl |
| 90 | 3-thienyl(cPr)CH | 2,5-diCl-phenyl |
| 91 | 2-isoxazolyl(cPr)CH | 2,5-diCl-phenyl |
| 92 | 2-(5-CH₃-furanyl)(cPr)CH | 2,5-diCl-phenyl |
| 93 | 2-(4-CH₃-isoxazolyl)(cPr)CH | 2,5-diCl-phenyl |
| 94 | cPr-CH(CH₃) | 2,5-diCl-phenyl |
| 95 | 1-cPr-CH(CH₂CH₃) | 2,5-diCl-phenyl |
| 96 | 1-cPr-CH(CH₂CH₂CH₃) | 2,5-diCl-phenyl |
| 97 | 1-cPr-CH(CH₂OCH₃) | 2,5-diCl-phenyl |
| 98 | 1-cPr-CH(CH₂CH₂OCH₃) | 2,5-diCl-phenyl |
| 99 | (cBu)₂CH | 2,5-diCl-phenyl |
| 100 | phenyl(cBu)CH | 2,5-diCl-phenyl |
| 101 | 2-furanyl(cBu)CH | 2,5-diCl-phenyl |
| 102 | 3-furan(cBu)CH | 2,5-diCl-phenyl |
| 103 | 2-thienyl (cBu)CH | 2,5-diCl-phenyl |
| 104 | 3-thienyl(cBu)CH | 2,5-diCl-phenyl |
| 105 | 2-isoxazolyl(cBu)CH | 2,5-diCl-phenyl |
| 106 | 2-(5-CH₃-furanyl)(cBu)CH | 2,5-diCl-phenyl |
| 107 | 2-(4-CH₃-isoxazolyl)(cBu)CH | 2,5-diCl-phenyl |
| 108 | cBu-CH(CH₃) | 2,5-diCl-phenyl |
| 109 | 1-cBu-CH(CH₂CH₃) | 2,5-diCl-phenyl |
| 110 | 1-cBu-CH(CH₂CH₂CH₃) | 2,5-diCl-phenyl |
| 111 | 1-cBu-CH(CH₂OCH₃) | 2,5-diCl-phenyl |
| 112 | 1-cBu-CH(CH₂CH₂OCH₃) | 2,5-diCl-phenyl |
| 113 | (cPr)₂CH | 2-Cl-4-CF₃O-phenyl |
| 114 | phenyl(cPr) CH | 2-Cl-4-CF₃O-phenyl |
| 115 | 2-furanyl(cPr)CH | 2-Cl-4-CF₃O-phenyl |
| 116 | 3-furan(cPr)CH | 2-Cl-4-CF₃O-phenyl |
| 117 | 2-thienyl(cPr)CH | 2-Cl-4-CF₃O-phenyl |
| 118 | 3-thienyl(cPr)CH | 2-Cl-4-CF₃O-phenyl |
| 119 | 2-isoxazolyl(cPr)CH | 2-Cl-4-CF₃O-phenyl |
| 120 | 2-(5-CH₃-furanyl)(cPr)CH | 2-Cl-4-CF₃O-phenyl |
| 121 | 2-(4-CH₃-isoxazolyl)(cPr)CH | 2-Cl-4-CF₃O-phenyl |
| 122 | cPr-CH(CH₃) | 2-Cl-4-CF₃O-phenyl |
| 123 | 1-cPr-CH(CH₂CH₃) | 2-Cl-4-CF₃O-phenyl |
| 124 | 1-cPr-CH(CH₂CH₂CH₃) | 2-Cl-4-CF₃O-phenyl |
| 125 | 1-cPr-CH(CH₂OCH₃) | 2-Cl-4-CF₃O-phenyl |
| 126 | 1-cPr-CH(CH₂CH₂OCH₃) | 2-Cl-4-CF₃O-phenyl |
| 127 | (cBu)₂CH | 2-Cl-4-CF₃O-phenyl |
| 128 | phenyl(cBu)CH | 2-Cl-4-CF₃O-phenyl |
| 129 | 2-furanyl(cBu)CH | 2-Cl-4-CF₃O-phenyl |
| 130 | 3-furan(cBu)CH | 2-Cl-4-CF₃O-phenyl |
| 131 | 2-thienyl(cBu)CH | 2-Cl-4-CF₃O-phenyl |
| 132 | 3-thienyl(cBu)CH | 2-Cl-4-CF₃O-phenyl |
| 133 | 2-isoxazolyl(cBu)CH | 2-Cl-4-CF₃O-phenyl |
| 134 | 2-(5-CH₃-furanyl)(cBu)CH | 2-Cl-4-CF₃O-phenyl |
| 135 | 2-(4-CH₃-isoxazolyl)(cBu)CH | 2-Cl-4-CF₃O-phenyl |
| 136 | cBu-CH(CH₃) | 2-Cl-4-CF₃O-phenyl |
| 137 | 1-cBu-CH(CH₂CH₃) | 2-Cl-4-CF₃O-phenyl |
| 138 | 1-cBu-CH(CH₂CH₂CH₃) | 2-Cl-4-CF₃O-phenyl |
| 139 | 1-cBu-CH(CH₂OCH₃) | 2-Cl-4-CF₃O-phenyl |

TABLE 3-continued

| | | |
|---|---|---|
| 140 | 1-cBu-CH(CH$_2$CH$_2$OCH$_3$) | 2-Cl-4-CF$_3$O-phenyl |
| 141 | (cPr)$_2$CH | 2-Cl-4-CH$_3$-phenyl |
| 142 | phenyl(cPr)CH | 2-Cl-4-CH$_3$-phenyl |
| 143 | 2-furanyl(cPr)CH | 2-Cl-4-CH$_3$-phenyl |
| 144 | 3-furan(cPr)CH | 2-Cl-4-CH$_3$-phenyl |
| 145 | 2-thienyl(cPr)CH | 2-Cl-4-CH$_3$-phenyl |
| 146 | 3-thienyl(cPr)CH | 2-Cl-4-CH$_3$-phenyl |
| 147 | 2-isoxazoly1(cPr)CH | 2-Cl-4-CH$_3$-phenyl |
| 148 | 2-(5-CH$_3$-furanyl)(cPr)CH | 2-Cl-4-CH$_3$-phenyl |
| 149 | 2-(4-CH$_3$-isoxazolyl)(cPr)CH | 2-Cl-4-CH$_3$-phenyl |
| 150 | cPr-CH(CH$_3$) | 2-Cl-4-CH$_3$-phenyl |
| 151 | 1-cPr-CH(CH$_2$CH$_3$) | 2-Cl-4-CH$_3$-phenyl |
| 152 | 1-cPr-CH(CH$_2$CH$_2$CH$_3$) | 2-Cl-4-CH$_3$-phenyl |
| 153 | 1-cPr-CH(CH$_2$OCH$_3$) | 2-Cl-4-CH$_3$-phenyl |
| 154 | 1-cPr-CH(CH$_2$CH$_2$OCH$_3$) | 2-Cl-4-CH$_3$-phenyl |
| 155 | (cBu)$_2$CH | 2-Cl-4-CH$_3$-phenyl |
| 156 | phenyl(cBu)CH | 2-Cl-4-CH$_3$-phenyl |
| 157 | 2-furanyl(cBu)CH | 2-Cl-4-CH$_3$-phenyl |
| 158 | 3-furan(cBu)CH | 2-Cl-4-CH$_3$-phenyl |
| 159 | 2-thienyl(cBu)CH | 2-Cl-4-CH$_3$-phenyl |
| 160 | 3-thienyl(cBu)CH | 2-Cl-4-CH$_3$-phenyl |
| 161 | 2-isoxazolyl(cBu)CH | 2-Cl-4-CH$_3$-phenyl |
| 162 | 2-(5-CH$_3$-furanyl)(cBu)CH | 2-Cl-4-CH$_3$-phenyl |
| 163 | 2-(4-CH$_3$-isoxazolyl)(cBu)CH | 2-Cl-4-CH$_3$-phenyl |
| 164 | cBu-CH(CH$_3$) | 2-Cl-4-CH$_3$-phenyl |
| 165 | 1-cBu-CH(CH$_2$CH$_3$) | 2-Cl-4-CH$_3$-phenyl |
| 166 | 1-cBu-CH(CH$_2$CH$_2$CH$_3$) | 2-Cl-4-CH$_3$-phenyl |
| 167 | 1-cBu-CH(CH$_2$OCH$_3$) | 2-Cl-4-CH$_3$-phenyl |
| 168 | 1-cBu-CH(CH$_2$CH$_2$OCH$_3$) | 2-Cl-4-CH$_3$-phenyl |
| 169 | (cPr)$_2$CH | 2-Cl-4-CN-phenyl |
| 170 | phenyl(cPr)CH | 2-Cl-4-CN-phenyl |
| 171 | 2-furanyl(cPr)CH | 2-Cl-4-CN-phenyl |
| 172 | 3-furan(cPr)CH | 2-Cl-4-CN-phenyl |
| 173 | 2-thienyl(cPr)CH | 2-Cl-4-CN-phenyl |
| 174 | 3-thienyl(cPr)CH | 2-Cl-4-CN-phenyl |
| 175 | 2-isoxazolyl(cPr)CH | 2-Cl-4-CN-phenyl |
| 176 | 2-(5-CH$_3$-furanyl)(cPr)CH | 2-Cl-4-CN-phenyl |
| 177 | 2-(4-CH$_3$-isoxazolyl)(cPr)CH | 2-Cl-4-CN-phenyl |
| 178 | cPr-CH(CH$_3$) | 2-Cl-4-CN-phenyl |
| 179 | 1-cPr-CH(CH$_2$CH$_3$) | 2-Cl-4-CN-phenyl |
| 180 | 1-cPr-CH(CH$_2$CH$_2$CH$_3$) | 2-Cl-4-CN-phenyl |
| 181 | 1-cPr-CH(CH$_2$OCH$_3$) | 2-Cl-4-CN-phenyl |
| 182 | 1-cPr-CH(CH$_2$CH$_2$OCH$_3$) | 2-Cl-4-CN-phenyl |
| 183 | (cBu)$_2$CH | 2-Cl-4-CN-phenyl |
| 184 | phenyl(cBu)CH | 2-Cl-4-CN-phenyl |
| 185 | 2-furanyl(cBu)CH | 2-Cl-4-CN-phenyl |
| 186 | 3-furan(cBu)CH | 2-Cl-4-CN-phenyl |
| 187 | 2-thienyl(cBu)CH | 2-Cl-4-CN-phenyl |
| 188 | 3-thienyl(cBu)CH | 2-Cl-4-CN-phenyl |
| 189 | 2-isoxazolyl(cBu)CH | 2-Cl-4-CN-phenyl |
| 190 | 2-(5-CH$_3$-furanyl)(cBu)CH | 2-Cl-4-CN-phenyl |
| 191 | 2-(4-CH$_3$-isoxazolyl)(cBu)CH | 2-Cl-4-CN-phenyl |
| 192 | cBu-CH(CH$_3$) | 2-Cl-4-CN-phenyl |
| 193 | 1-cBu-CH(CH$_2$CH$_3$) | 2-Cl-4-CN-phenyl |
| 194 | 1-cBu-CH(CH$_2$CH$_2$CH$_3$) | 2-Cl-4-CN-phenyl |
| 195 | 1-cBu-CH(CH$_2$OCH$_3$) | 2-Cl-4-CN-phenyl |
| 196 | 1-cBu-CH(CH$_2$CH$_2$OCH$_3$) | 2-Cl-4-CN-phenyl |
| 197 | (cPr)$_2$CH | 2-CF$_3$-4-Cl-phenyl |
| 198 | phenyl(cPr)CH | 2-CF$_3$-4-Cl-phenyl |
| 199 | 2-furanyl(cPr)CH | 2-CF$_3$-4-Cl-phenyl |
| 200 | 3-furan(cPr)CH | 2-CF$_3$-4-Cl-phenyl |
| 201 | 2-thienyl(cPr)CH | 2-CF$_3$-4-Cl-phenyl |
| 202 | 3-thienyl(cPr)CH | 2-CF$_3$-4-Cl-phenyl |
| 203 | 2-isoxazolyl(cPr)CH | 2-CF$_3$-4-Cl-phenyl |
| 204 | 2-(5-CH$_3$-furanyl)(cPr)CH | 2-CF$_3$-4-Cl-phenyl |
| 205 | 2-(4-CH$_3$-isoxazolyl)(cPr)CH | 2-CF$_3$-4-Cl-phenyl |
| 206 | cPr-CH(CH$_3$) | 2-CF$_3$-4-Cl-phenyl |
| 207 | 1-cPr-CH(CH$_2$CH$_3$) | 2-CF$_3$-4-Cl-phenyl |
| 208 | 1-cPr-CH(CH$_2$CH$_2$CH$_3$) | 2-CF$_3$-4-Cl-phenyl |
| 209 | 1-cPr-CH(CH$_2$OCH$_3$) | 2-CF$_3$-4-Cl-phenyl |
| 210 | 1-cPr-CH(CH$_2$CH$_2$OCH$_3$) | 2-CF$_3$-4-Cl-phenyl |
| 211 | (cBu)$_2$CH | 2-CF$_3$-4-Cl-phenyl |
| 212 | phenyl(cBu)CH | 2-CF$_3$-4-Cl-phenyl |
| 213 | 2-furanyl(cBu)CH | 2-CF$_3$-4-Cl-phenyl |
| 214 | 3-furan(cBu)CH | 2-CF$_3$-4-Cl-phenyl |
| 215 | 2-thienyl(cBu)CH | 2-CF$_3$-4-Cl-phenyl |
| 216 | 3-thienyl(cBu)CH | 2-CF$_3$-4-Cl-phenyl |
| 217 | 2-isoxazolyl(cBu)CH | 2-CF$_3$-4-Cl-phenyl |
| 218 | 2-(5-CH$_3$-furanyl)(cBu)CH | 2-CF$_3$-4-Cl-phenyl |
| 219 | 2-(4-CH$_3$-isoxazolyl)(cBu)CH | 2-CF$_3$-4-Cl-phenyl |
| 220 | cBu-CH(CH$_3$) | 2-CF$_3$-4-Cl-phenyl |
| 221 | 1-cBu-CH(CH$_2$CH$_3$) | 2-CF$_3$-4-Cl-phenyl |
| 222 | 1-cBu-CH(CH$_2$CH$_2$CH$_3$) | 2-CF$_3$-4-Cl-phenyl |
| 223 | 1-cBu-CH(CH$_2$OCH$_3$) | 2-CF$_3$-4-Cl-phenyl |
| 224 | 1-cBu-CH(CH$_2$CH$_2$OCH$_3$) | 2-CF$_3$-4-Cl-phenyl |
| 225 | (cPr)$_2$CH | 2-CF$_3$-4-MeO-phenyl |
| 226 | phenyl(cPr)CH | 2-CF$_3$-4-MeO-phenyl |
| 227 | 2-furanyl(cPr)CH | 2-CF$_3$-4-MeO-phenyl |
| 228 | 3-furan(cPr)CH | 2-CF$_3$-4-MeO-phenyl |
| 229 | 2-thienyl(cPr)CH | 2-CF$_3$-4-MeO-phenyl |
| 230 | 3-thienyl(cPr)CH | 2-CF$_3$-4-MeO-phenyl |
| 231 | 2-isoxazolyl(cPr)CH | 2-CF$_3$-4-MeO-phenyl |
| 232 | 2-(5-CH$_3$-furanyl)(cPr)CH | 2-CF$_3$-4-MeO-phenyl |
| 233 | 2-(4-CH$_3$-isoxazolyl)(cPr)CH | 2-CF$_3$-4-MeO-phenyl |
| 234 | cPr-CH(CH$_3$) | 2-CF$_3$-4-MeO-phenyl |
| 235 | 1-cPr-CH(CH$_2$CH$_3$) | 2-CF$_3$-4-MeO-phenyl |
| 236 | 1-cPr-CH(CH$_2$CH$_2$CH$_3$) | 2-CF$_3$-4-MeO-phenyl |
| 237 | 1-cPr-CH(CH$_2$OCH$_3$) | 2-CF$_3$-4-MeO-phenyl |
| 238 | 1-cPr-CH(CH$_2$CH$_2$OCH$_3$) | 2-CF$_3$-4-MeO-phenyl |
| 239 | (cBu)$_2$CH | 2-CF$_3$-4-MeO-phenyl |
| 240 | phenyl(cBu)CH | 2-CF$_3$-4-MeO-phenyl |
| 241 | 2-furanyl(cBu)CH | 2-CF$_3$-4-MeO-phenyl |
| 242 | 3-furan(cBu)CH | 2-CF$_3$-4-MeO-phenyl |
| 243 | 2-thienyl(cBu)CH | 2-CF$_3$-4-MeO-phenyl |
| 244 | 3-thienyl(cBu)CH | 2-CF$_3$-4-MeO-phenyl |
| 245 | 2-isoxazolyl(cBu)CH | 2-CF$_3$-4-MeO-phenyl |
| 246 | 2-(5-CH$_3$-furanyl)(cBu)CH | 2-CF$_3$-4-MeO-phenyl |
| 247 | 2-(4-CH$_3$-isoxazolyl)(cBu)CH | 2-CF$_3$-4-MeO-phenyl |
| 248 | cBu-CH(CH$_3$) | 2-CF$_3$-4-MeO-phenyl |
| 249 | 1-cBu-CH(CH$_2$CH$_3$) | 2-CF$_3$-4-MeO-phenyl |
| 250 | 1-cBu-CH(CH$_2$CH$_2$CH$_3$) | 2-CF$_3$-4-MeO-phenyl |
| 251 | 1-cBu-CH(CH$_2$OCH$_3$) | 2-CF$_3$-4-MeO-phenyl |
| 252 | 1-cBu-CH(CH$_2$CH$_2$OCH$_3$) | 2-CF$_3$-4-MeO-phenyl |
| 253 | (cPr)$_2$CH | 2-CF$_3$-4-n-PrO-phenyl |
| 254 | phenyl(cPr)CH | 2-CF$_3$-4-n-PrO-phenyl |
| 255 | 2-furanyl(cPr)CH | 2-CF$_3$-4-n-PrO-phenyl |
| 256 | 3-furan(cPr)CH | 2-CF$_3$-4-n-PrO-phenyl |
| 257 | 2-thienyl(cPr)CH | 2-CF$_3$-4-n-PrO-phenyl |
| 258 | 3-thienyl(cPr)CH | 2-CF$_3$-4-n-PrO-phenyl |
| 259 | 2-isoxazolyl(cPr)CH | 2-CF$_3$-4-n-PrO-phenyl |
| 260 | 2-(5-CH$_3$-furanyl)(cPr)CH | 2-CF$_3$-4-n-PrO-phenyl |
| 261 | 2-(4-CH$_3$-isoxazolyl)(cPr)CH | 2-CF$_3$-4-n-PrO-phenyl |
| 262 | cPr-CH(CH$_3$) | 2-CF$_3$-4-n-PrO-phenyl |
| 263 | 1-cPr-CH(CH$_2$CH$_3$) | 2-CF$_3$-4-n-PrO-phenyl |
| 264 | 1-cPr-CH(CH$_2$CH$_2$CH$_3$) | 2-CF$_3$-4-n-PrO-phenyl |
| 265 | 1-cPr-CH(CH$_2$OCH$_3$) | 2-CF$_3$-4-n-PrO-phenyl |
| 266 | 1-cPr-CH(CH$_2$CH$_2$OCH$_3$) | 2-CF$_3$-4-n-PrO-phenyl |
| 267 | (cBu)$_2$CH | 2-CF$_3$-4-n-PrO-phenyl |
| 268 | phenyl(cBu)CH | 2-CF$_3$-4-n-PrO-phenyl |
| 269 | 2-furanyl(cBu)CH | 2-CF$_3$-4-n-PrO-phenyl |
| 270 | 3-furan(cBu)CH | 2-CF$_3$-4-n-PrO-phenyl |
| 271 | 2-thienyl(cBu)CH | 2-CF$_3$-4-n-PrO-phenyl |
| 272 | 3-thienyl(cBu)CH | 2-CF$_3$-4-n-PrO-phenyl |
| 273 | 2-isoxazolyl(cBu)CH | 2-CF$_3$-4-n-PrO-phenyl |
| 274 | 2-(5-CH$_3$-furanyl)(cBu)CH | 2-CF$_3$-4-n-PrO-phenyl |
| 275 | 2-(4-CH$_3$-isoxazolyl)(cBu)CH | 2-CF$_3$-4-n-PrO-phenyl |
| 276 | cBu-CH(CH$_3$) | 2-CF$_3$-4-n-PrO-phenyl |
| 277 | 1-cBu-CH(CH$_2$CH$_3$) | 2-CF$_3$-4-n-PrO-phenyl |
| 278 | 1-cBu-CH(CH$_2$CH$_2$CH$_3$) | 2-CF$_3$-4-n-PrO-phenyl |
| 279 | 1-cBu-CH(CH$_2$OCH$_3$) | 2-CF$_3$-4-n-PrO-phenyl |
| 280 | 1-cBu-CH(CH$_2$CH$_2$OCH$_3$) | 2-CF$_3$-4-n-PrO-phenyl |
| 281 | (cPr)$_2$CH | 2,4-diCF$_3$-phenyl |
| 282 | phenyl(cPr)CH | 2,4-diCF$_3$-phenyl |
| 283 | 2-furanyl(cPr)CH | 2,4-diCF$_3$-phenyl |
| 284 | 3-furan(cPr)CH | 2,4-diCF$_3$-phenyl |
| 285 | 2-thienyl(cPr)CH | 2,4-diCF$_3$-phenyl |
| 286 | 3-thienyl(cPr)CH | 2,4-diCF$_3$-phenyl |
| 287 | 2-isoxazolyl(cPr)CH | 2,4-diCF$_3$-phenyl |
| 288 | 2-(5-CH$_3$-furanyl)(cPr)CH | 2,4-diCF$_3$-phenyl |
| 289 | 2-(4-CH$_3$-isoxazolyl)(cPr)CH | 2,4-diCF$_3$-phenyl |
| 290 | cPr-CH(CH$_3$) | 2,4-diCF$_3$-phenyl |
| 291 | 1-cPr-CH(CH$_2$CH$_3$) | 2,4-diCF$_3$-phenyl |
| 292 | 1-cPr-CH(CH$_2$CH$_2$CH$_3$) | 2,4-diCF$_3$-phenyl |
| 293 | 1-cPr-CH(CH$_2$OCH$_3$) | 2,4-diCF$_3$-phenyl |
| 294 | 1-cPr-CH(CH$_2$CH$_2$OCH$_3$) | 2,4-diCF$_3$-phenyl |
| 295 | (cBu)$_2$CH | 2,4-diCF$_3$-phenyl |
| 296 | phenyl(cBu)CH | 2,4-diCF$_3$-phenyl |
| 297 | 2-furanyl(cBu)CH | 2,4-diCF$_3$-phenyl |

TABLE 3-continued

| | | |
|---|---|---|
| 298 | 3-furan(cBu)CH | 2,4-diCF$_3$-phenyl |
| 299 | 2-thienyl(cBu)CH | 2,4-diCF$_3$-phenyl |
| 300 | 3-thienyl(cBu)CH | 2,4-dieF3-phenyl |
| 301 | 2-isoxazolyl(cBu)CH | 2,4-diCF$_3$-phenyl |
| 302 | 2-(5-CH$_3$-furanyl)(cBu)CH | 2,4-diCF$_3$-phenyl |
| 303 | 2-(4-CH$_3$-isoxazolyl)(cBu)CH | 2,4-diCF$_3$-phenyl |
| 304 | cBu-CH(CH$_3$) | 2,4-diCF$_3$-phenyl |
| 305 | 1-cBu-CH(CH$_2$CH$_3$) | 2,4-diCF$_3$-phenyl |
| 306 | 1-cBu-CH(CH$_2$CH$_2$CH$_3$) | 2,4-diCF$_3$-phenyl |
| 307 | 1-cBu-CH(CH$_2$OCH$_3$) | 2,4-diCF$_3$-phenyl |
| 308 | 1-cBu-CH(CH$_2$CH$_2$OCH$_3$) | 2,4-diCF$_3$-phenyl |
| 309 | (cPr)$_2$CH | 2-CF$_3$-4-F-phenyl |
| 310 | phenyl(cPr)CH | 2-CF$_3$-4-F-phenyl |
| 311 | 2-furanyl(cPr)CH | 2-CF$_3$-4-F-phenyl |
| 312 | 3-furan(cPr)CH | 2-CF$_3$-4-F-phenyl |
| 313 | 2-thienyl(cPr)CH | 2-CF$_3$-4-F-phenyl |
| 314 | 3-thienyl(cPr)CH | 2-CF$_3$-4-F-phenyl |
| 315 | 2-isoxazolyl(cPr)CH | 2-CF$_3$-4-F-phenyl |
| 316 | 2-(5-CH$_3$-furanyl)(cPr)CH | 2-CF$_3$-4-F-phenyl |
| 317 | 2-(4-CH$_3$-isoxazolyl)(cPr)CH | 2-CF$_3$-4-F-phenyl |
| 318 | cPr-CH(CH$_3$) | 2-CF$_3$-4-F-phenyl |
| 319 | 1-cPr-CH(CH$_2$CH$_3$) | 2-CF$_3$-4-F-phenyl |
| 320 | 1-cPr-CH(CH$_2$CH$_2$CH$_3$) | 2-CF$_3$-4-F-phenyl |
| 321 | 1-cPr-CH(CH$_2$OCH$_3$) | 2-CF$_3$-4-F-phenyl |
| 322 | 1-cPr-CH(CH$_2$CH$_2$OCH$_3$) | 2-CF$_3$-4-F-phenyl |
| 323 | (cBu)$_2$CH | 2-CF$_3$-4-F-phenyl |
| 324 | phenyl(cBu)CH | 2-CF$_3$-4-F-phenyl |
| 325 | 2-furanyl(cBu)CH | 2-CF$_3$-4-F-phenyl |
| 326 | 3-furan(cBu)CH | 2-CF$_3$-4-F-phenyl |
| 327 | 2-thienyl(cBu)CH | 2-CF$_3$-4-F-phenyl |
| 328 | 3-thienyl(cBu)CH | 2-CF$_3$-4-F-phenyl |
| 329 | 2-isoxazolyl(cBu)CH | 2-CF$_3$-4-F-phenyl |
| 330 | 2-(5-CH$_3$-furanyl)(cBu)CH | 2-CF$_3$-4-F-phenyl |
| 331 | 2-(4-CH$_3$-isoxazolyl)(cBu)CH | 2-CF$_3$-4-F-phenyl |
| 332 | cBu-CH(CH$_3$) | 2-CF$_3$-4-F-phenyl |
| 333 | 1-cBu-CH(CH$_2$CH$_3$) | 2-CF$_3$-4-F-phenyl |
| 334 | 1-cBu-CH(CH$_2$CH$_2$CH$_3$) | 2-CF$_3$-4-F-phenyl |
| 335 | 1-cBu-CH(CH$_2$OCH$_3$) | 2-CF$_3$-4-F-phenyl |
| 336 | 1-cBu-CH(CH$_2$CH$_2$OCH$_3$) | 2-CF$_3$-4-F-phenyl |
| 337 | (cPr)$_2$CH | 2-CH$_3$-4-Cl-pheriyl |
| 338 | phenyl(cPr)CH | 2-CH$_3$-4-Cl-phenyl |
| 339 | 2-furanyl(cPr)CH | 2-CH$_3$-4-Cl-phenyl |
| 340 | 3-furan(cPr)CH | 2-CH$_3$-4-Cl-phenyl |
| 341 | 2-thienyl(cPr)CH | 2-CH$_3$-4-Cl-phenyl |
| 342 | 3-thienyl(cPr)CH | 2-CH$_3$-4-Cl-phenyl |
| 343 | 2-isoxazolyl(cPr)CH | 2-CH$_3$-4-Cl-phenyl |
| 344 | 2-(5-CH$_3$-furanyl)(cPr)CH | 2-CH$_3$-4-Cl-phenyl |
| 345 | 2-(4-CH$_3$-isoxazolyl)(cPr)CH | 2-CH$_3$-4-Cl-phenyl |
| 346 | cPr-CH(CH$_3$) | 2-CH$_3$-4-Cl-phenyl |
| 347 | 1-cPr-CH(CH$_2$CH$_3$) | 2-CH$_3$-4-Cl-phenyl |
| 348 | 1-cPr-CH(CH$_2$CH$_2$CH$_3$) | 2-CH$_3$-4-Cl-phenyl |
| 349 | 1-cPr-CH(CH$_2$OCH$_3$) | 2-CH$_3$-4-Cl-phenyl |
| 350 | 1-cPr-CH(CH$_2$CH$_2$OCH$_3$) | 2-CH$_3$-4-Cl-phenyl |
| 351 | (cBu)$_2$CH | 2-CH$_3$-4-Cl-phenyl |
| 352 | phenyl(cBu)CH | 2-CH$_3$-4-Cl-phenyl |
| 353 | 2-furanyl(cBu)CH | 2-CH$_3$-4-Cl-phenyl |
| 354 | 3-furan(cBu)CH | 2-CH$_3$-4-Cl-phenyl |
| 355 | 2-thienyl(cBu)CH | 2-CH$_3$-4-Cl-phenyl |
| 356 | 3-thienyl(cBu)CH | 2-CH$_3$-4-Cl-phenyl |
| 357 | 2-isoxazolyl(cBu)CH | 2-CH$_3$-4-Cl-phenyl |
| 358 | 2-(5-CH$_3$-furanyl)(cBu)CH | 2-CH$_3$-4-Cl-phenyl |
| 359 | 2-(4-CH$_3$-isoxazolyl)(cBu)CH | 2-CH$_3$-4-Cl-phenyl |
| 360 | cBu-CH(CH$_3$) | 2-CH$_3$-4-Cl-phenyl |
| 361 | 1-cBu-CH(CH$_2$CH$_3$) | 2-CH$_3$-4-Cl-phenyl |
| 362 | 1-cBu-CH(CH$_2$CH$_2$CH$_3$) | 2-CH$_3$-4-Cl-phenyl |
| 363 | 1-cBu-CH(CH$_2$OCH$_3$) | 2-CH$_3$-4-Cl-phenyl |
| 364 | 1-cBu-CH(CH$_2$CH$_2$OCH$_3$) | 2-CH$_3$-4-Cl-phenyl |
| 365 | (cPr)$_2$CH | 2-CH$_3$-4-MeO-phenyl |
| 366 | phenyl(cPr)CH | 2-CH$_3$-4-MeO-phenyl |
| 367 | 2-furanyl(cPr)CH | 2-CH$_3$-4-MeO-phenyl |
| 368 | 3-furan(cPr)CH | 2-CH$_3$-4-MeO-phenyl |
| 369 | 2-thienyl(cPr)CH | 2-CH$_3$-4-MeO-phenyl |
| 370 | 3-thienyl(cPr)CH | 2-CH$_3$-4-MeO-phenyl |
| 371 | 2-isoxazolyl(cPr)CH | 2-CH$_3$-4-MeO-phenyl |
| 372 | 2-(5-CH$_3$-furanyl)(cPr)CH | 2-CH$_3$-4-MeO-phenyl |
| 373 | 2-(4-CH$_3$-isoxazolyl)(cPr)CH | 2-CH$_3$-4-MeO-phenyl |
| 374 | cPr-CH(CH$_3$) | 2-CH$_3$-4-MeO-phenyl |
| 375 | 1-cPr-CH(CH$_2$CH$_3$) | 2-CH$_3$-4-MeO-phenyl |
| 376 | 1-cPr-CH(CH$_2$CH$_2$CH$_3$) | 2-CH$_3$-4-MeO-phenyl |
| 377 | 1-cPr-CH(CH$_2$OCH$_3$) | 2-CH$_3$-4-MeO-phenyl |
| 378 | 1-cPr-CH(CH$_2$CH$_2$OCH$_3$) | 2-CH$_3$-4-MeO-phenyl |
| 379 | (cBu)$_2$CH | 2-CH$_3$-4-MeO-phenyl |
| 380 | phenyl(cBu)CH | 2-CH$_3$-4-MeO-phenyl |
| 381 | 2-furanyl(cBu)CH | 2-CH$_3$-4-MeO-phenyl |
| 382 | 3-furan(cBu)CH | 2-CH$_3$-4-MeO-phenyl |
| 383 | 2-thienyl(cBu)CH | 2-CH$_3$-4-MeO-phenyl |
| 384 | 3-thienyl(cBu)CH | 2-CH$_3$-4-MeO-phenyl |
| 385 | 2-isoxazolyl(cBu)CH | 2-CH$_3$-4-MeO-phenyl |
| 386 | 2-(5-CH$_3$-furanyl)(cBu)CH | 2-CH$_3$-4-MeO-phenyl |
| 387 | 2-(4-CH$_3$-isoxazolyl)(cBu)CH | 2-CH$_3$-4-MeO-phenyl |
| 388 | cBu-CH(CH$_3$) | 2-CH$_3$-4-MeO-phenyl |
| 389 | 1-cBu-CH(CH$_2$CH$_3$) | 2-CH$_3$-4-MeO-phenyl |
| 390 | 1-cBu-CH(CH$_2$CH$_2$CH$_3$) | 2-CH$_3$-4-MeO-phenyl |
| 391 | 1-cBu-CH(CH$_2$OCH$_3$) | 2-CH$_3$-4-MeO-phenyl |
| 392 | 1-cBu-CH(CH$_2$CH$_2$OCH$_3$) | 2-CH$_3$-4-MeO-phenyl |
| 393 | (cPr)$_2$CH | 2,4-diCH$_3$-phenyl |
| 394 | phenyl(cPr)CH | 2,4-diCH$_3$-phenyl |
| 395 | 2-furanyl(cPr)CH | 2,4-diCH$_3$-phenyl |
| 396 | 3-furan(cPr)CH | 2,4-diCH$_3$-phenyl |
| 397 | 2-thienyl(cPr)CH | 2,4-diCH$_3$-phenyl |
| 398 | 3-thienyl(cPr)CH | 2,4-diCH$_3$-phenyl |
| 399 | 2-isoxazolyl(cPr)CH | 2,4-diCH$_3$-phenyl |
| 400 | 2-(5-CH$_3$-furanyl)(cPr)CH | 2,4-diCH$_3$-phenyl |
| 401 | 2-(4-CH$_3$-isoxazolyl)(cPr)CH | 2,4-diCH$_3$-phenyl |
| 402 | cPr-CH(CH$_3$) | 2,4-diCH$_3$-phenyl |
| 403 | 1-cPr-CH(CH$_2$CH$_3$) | 2,4-diCH$_3$-phenyl |
| 404 | 1-cPr-CH(CH$_2$CH$_2$CH$_3$) | 2,4-diCH$_3$-phenyl |
| 405 | 1-cPr-CH(CH$_2$OCH$_3$) | 2,4-diCH$_3$-phenyl |
| 406 | 1-cPr-CH(CH$_2$CH$_2$OCH$_3$) | 2,4-diCH$_3$-phenyl |
| 407 | (cBu)$_2$CH | 2,4-diCH$_3$-phenyl |
| 408 | phenyl(cBu)CH | 2,4-diCH$_3$-phenyl |
| 409 | 2-furanyl(cBu)CH | 2,4-diCH$_3$-phenyl |
| 410 | 3-furan(cBu)CH | 2,4-diCH$_3$-phenyl |
| 411 | 2-thienyl(cBu)CH | 2,4-diCH$_3$-phenyl |
| 412 | 3-thienyl(cBu)CH | 2,4-diCH$_3$-phenyl |
| 413 | 2-isoxazolyl(cBu)CH | 2,4-diCH$_3$-phenyl |
| 414 | 2-(5-CH$_3$-furanyl)(cBu)CH | 2,4-diCH$_3$-phenyl |
| 415 | 2-(4-CH$_3$-isoxazolyl)(cBu)CH | 2,4-diCH$_3$-phenyl |
| 416 | cBu-CH(CH$_3$) | 2,4-diCH$_3$-phenyl |
| 417 | 1-cBu-CH(CH$_2$CH$_3$) | 2,4-diCH$_3$-phenyl |
| 418 | 1-cBu-CH(CH$_2$CH$_2$CH$_3$) | 2,4-diCH$_3$-phenyl |
| 419 | 1-cBu-CH(CH$_2$OCH$_3$ | 2,4-diCH$_3$-phenyl |
| 420 | 1-cBu-CH(CH$_2$CH$_2$OCH$_3$) | 2,4-diCH$_3$-phenyl |
| 421 | (cPr)$_2$CH | 2-CH$_3$-4-(CH$_3$)$_2$N-phenyl |
| 422 | phenyl(cPr)CH | 2-CH$_3$-4-(CH$_3$)$_2$N-phenyl |
| 423 | 2-furanyl(cPr)CH | 2-CH$_3$-4-(CH$_3$)$_2$N-phenyl |
| 424 | 3-furan(cPr)CH | 2-CH$_3$-4-(CH$_3$)$_2$N-phenyl |
| 425 | 2-thienyl(cPr)CH | 2-CH$_3$-4-(CH$_3$)$_2$N-phenyl |
| 426 | 3-thienyl(cPr)CH | 2-CH$_3$-4-(CH$_3$)$_2$N-phenyl |
| 427 | 2-isoxazolyl(cPr)CH | 2-CH$_3$-4-(CH$_3$)$_2$N-phenyl |
| 428 | 2-(5-CH$_3$-furanyl)(cPr)CH | 2-CH$_3$-4-(CH$_3$)$_2$N-phenyl |
| 429 | 2-(4-CH$_3$-isoxazolyl)(cPr)CH | 2-CH$_3$-4-(CH$_3$)$_2$N-phenyl |
| 430 | cPr-CH(CH$_3$) | 2-CH$_3$-4-(CH$_3$)$_2$N-phenyl |
| 431 | 1-cPr-CH(CH$_2$CH$_3$) | 2-CH$_3$-4-(CH$_3$)$_2$N-phenyl |
| 432 | 1-cPr-CH(CH$_2$CH$_2$CH$_3$) | 2-CH$_3$-4-(CH$_3$)$_2$N-phenyl |
| 433 | 1-cPr-CH(CH$_2$OCH$_3$) | 2-CH$_3$-4-(CH$_3$)$_2$N-phenyl |
| 434 | 1-cPr-CH(CH$_2$CH$_2$OCH$_3$) | 2-CH$_3$-4-(CH$_3$)$_2$N-phenyl |
| 435 | (cBu)$_2$CH | 2-CH$_3$-4-(CH$_3$)$_2$N-phenyl |
| 436 | phenyl(cBu)CH | 2-CH$_3$-4-(CH$_3$)$_2$N-phenyl |
| 437 | 2-furanyl(cBu)CH | 2-CH$_3$-4-(CH$_3$)$_2$N-phenyl |
| 438 | 3-furan(cBu)CH | 2-CH$_3$-4-(CH$_3$)$_2$N-phenyl |
| 439 | 2-thienyl(cBu)CH | 2-CH$_3$-4-(CH$_3$)$_2$N-phenyl |
| 440 | 3-thienyl(cBu)CH | 2-CH$_3$-4-(CH$_3$)$_2$N-phenyl |
| 441 | 2-isoxazolyl(cBu)CH | 2-CH$_3$-4-(CH$_3$)$_2$N-phenyl |
| 442 | 2-(5-CH$_3$-furanyl)(cBu)CH | 2-CH$_3$-4-(CH$_3$)$_2$N-phenyl |
| 443 | 2-(4-CH$_3$-isoxazolyl)(cBu)CH | 2-CH$_3$-4-(CH$_3$)$_2$N-phenyl |
| 444 | cBu-CH(CH$_3$) | 2-CH$_3$-4-(CH$_3$)$_2$N-phenyl |
| 445 | 1-cBu-CH(CH$_2$CH$_3$) | 2-CH$_3$-4-(CH$_3$)$_2$N-phenyl |
| 446 | 1-cBu-CH(CH$_2$CH$_2$CH$_3$) | 2-CH$_3$-4-(CH$_3$)$_2$N-phenyl |
| 447 | 1-cBu-CH(CH$_2$OCH$_3$) | 2-CH$_3$-4-(CH$_3$)$_2$N-phenyl |
| 448 | 1-cBu-CH(CH$_2$CH$_2$OCH$_3$) | 2-CH$_3$-4-(CH$_3$)$_2$N-phenyl |
| 449 | (cPr)$_2$CH | 2-MeO-4-CH$_3$-phenyl |
| 450 | phenyl(cPr)CH | 2-MeO-4-CH$_3$-phenyl |
| 451 | 2-furanyl(cPr)CH | 2-MeO-4-CH$_3$-phenyl |
| 452 | 3-furan(cPr)CH | 2-MeO-4-CH$_3$-phenyl |
| 453 | 2-thienyl(cPr)CH | 2-MeO-4-CH$_3$-phenyl |
| 454 | 3-thienyl(cPr)CH | 2-MeO-4-CH$_3$-phenyl |
| 455 | 2-isoxazolyl(cPr)CH | 2-MeO-4-CH$_3$-phenyl |

TABLE 3-continued

| | | |
|---|---|---|
| 456 | 2-(5-CH₃-furanyl)(cPr)CH | 2-MeO-4-CH₃-phenyl |
| 457 | 2-(4-CH₃-isoxazolyl)(cPr)CH | 2-MeO-4-CH₃-phenyl |
| 458 | cPr-CH(CH₃) | 2-MeO-4-CH₃-phenyl |
| 459 | 1-cPr-CH(CH₂CH₃) | 2-MeO-4-CH₃-phenyl |
| 460 | 1-cPr-CH(CH₂CH₂CH₃) | 2-MeO-4-CH₃-phenyl |
| 461 | 1-cPr-CH(CH₂OCH₃) | 2-MeO-4-CH₃-phenyl |
| 462 | 1-cPr-CH(CH₂CH₂OCH₃) | 2-MeO-4-CH₃-phenyl |
| 463 | (cBu)₂CH | 2-MeO-4-CH₃-phenyl |
| 464 | phenyl(cBu)CH | 2-MeO-4-CH₃-phenyl |
| 465 | 2-furanyl(cBu)CH | 2-MeO-4-CH₃-phenyl |
| 466 | 3-furan(cBu)CH | 2-MeO-4-CH₃-phenyl |
| 467 | 2-thienyl(cBu)CH | 2-MeO-4-CH₃-phenyl |
| 468 | 3-thienyl(cBu)CH | 2-MeO-4-CH₃-phenyl |
| 469 | 2-isoxazolyl(cBu)CH | 2-MeO-4-CH₃-phenyl |
| 470 | 2-(5-CH₃-furanyl)(cBu)CH | 2-MeO-4-CH₃-phenyl |
| 471 | 2-(4-CH₃-isoxazolyl)(cBu)CH | 2-MeO-4-CH₃-phenyl |
| 472 | cBu-CH(CH₃) | 2-MeO-4-CH₃-phenyl |
| 473 | 1-cBu-CH(CH₂CH3) | 2-MeO-4-CH₃-phenyl |
| 474 | 1-cBu-CH(CH₂CH₂CH₃) | 2-MeO-4-CH₃-phenyl |
| 475 | 1-cBu-CH(CH₂OCH₃) | 2-MeO-4-CH₃-phenyl |
| 476 | 1-cBu-CH(CH₂CH₂OCH₃) | 2-MeO-4-CH₃-phenyl |
| 477 | (cPr)₂CH | 2-MeO-4-CF₃-phenyl |
| 478 | phenyl(cPr)CH | 2-MeO-4-CF₃-phenyl |
| 479 | 2-furanyl(cPr)CH | 2-MeO-4-CF₃-phenyl |
| 480 | 3-furan(cPr)CH | 2-MeO-4-CF₃-phenyl |
| 481 | 2-thienyl(cPr)CH | 2-MeO-4-CF₃-phenyl |
| 482 | 3-thienyl(cPr)CH | 2-MeO-4-CF₃-phenyl |
| 483 | 2-isoxazolyl(cPr)CH | 2-MeO-4-CF₃-phenyl |
| 484 | 2-(5-CH₃-furanyl)(cPr)CH | 2-MeO-4-CF₃-phenyl |
| 485 | 2-(4-CH₃-isoxazolyl)(cPr)CH | 2-MeO-4-CF₃-phenyl |
| 486 | cPr-CH(CH₃) | 2-MeO-4-CF₃-phenyl |
| 487 | 1-cPr-CH(CH₂CH₃) | 2-MeO-4-CF₃-phenyl |
| 488 | 1-cPr-CH(CH₂CH₂CH₃) | 2-MeO-4-CF₃-phenyl |
| 489 | 1-cPr-CH(CH₂OCH₃) | 2-MeO-4-CF₃-phenyl |
| 490 | 1-cPr-CH(CH₂CH₂OCH₃) | 2-MeO-4-CF₃-phenyl |
| 491 | (cBu)₂CH | 2-MeO-4-CF₃-phenyl |
| 492 | phenyl(cBu)CH | 2-MeO-4-CF₃-phenyl |
| 493 | 2-furanyl(cBu)CH | 2-MeO-4-CF₃-phenyl |
| 494 | 3-furan(cBu)CH | 2-MeO-4-CF₃-phenyl |
| 495 | 2-thienyl(cBu)CH | 2-MeO-4-CF₃-phenyl |
| 496 | 3-thienyl(cBu)CH | 2-MeO-4-CF₃-phenyl |
| 497 | 2-isoxazolyl(cBu)CH | 2-MeO-4-CF₃-phenyl |
| 498 | 2-(5-CH₃-furanyl)(cBu)CH | 2-MeO-4-CF₃-phenyl |
| 499 | 2-(4-CH₃-isoxazolyl)(cBu)CH | 2-MeO-4-CF₃-phenyl |
| 500 | cBu-CH(CH₃) | 2-MeO-4-CF₃-phenyl |
| 501 | 1-cBu-CH(CH₂CH₃) | 2-MeO-4-CF₃-phenyl |
| 502 | 1-cBu-CH(CH₂CH₂CH₃) | 2-MeO-4-CF₃-phenyl |
| 503 | 1-cBu-CH(CH₂OCH₃) | 2-MeO-4-CF₃-phenyl |
| 504 | 1-cBu-CH(CH₂CH₂OCH₃) | 2-MeO-4-CF₃-phenyl |
| 505 | (cPr)₂CH | 2-MeO-4-Cl-phenyl |
| 506 | phenyl(cPr)CH | 2-MeO-4-Cl-phenyl |
| 507 | 2-furanyl(cPr)CH | 2-MeO-4-Cl-phenyl |
| 508 | 3-furan(cPr)CH | 2-MeO-4-Cl-phenyl |
| 509 | 2-thienyl(cPr)CH | 2-MeO-4-Cl-phenyl |
| 510 | 3-thienyl(cPr)CH | 2-MeO-4-Cl-phenyl |
| 511 | 2-isoxazolyl(cPr)CH | 2-MeO-4-Cl-phenyl |
| 512 | 2-(5-CH₃-furanyl)(cPr)CH | 2-MeO-4-Cl-phenyl |
| 513 | 2-(4-CH₃-isoxazolyl)(cPr)CH | 2-MeO-4-Cl-phenyl |
| 514 | cPr-CH(CH₃) | 2-MeO-4-Cl-phenyl |
| 515 | 1-cPr-CH(CH₂CH₃) | 2-MeO-4-Cl-phenyl |
| 516 | 1-cPr-CH(CH₂CH₂CH₃) | 2-MeO-4-Cl-phenyl |
| 517 | 1-cPr-CH(CH₂OCH₃) | 2-MeO-4-Cl-phenyl |
| 518 | 1-cPr-CH(CH₂CH₂OCH₃) | 2-MeO-4-Cl-phenyl |
| 519 | (cBu)₂CH | 2-MeO-4-Cl-phenyl |
| 520 | phenyl(cBu)CH | 2-MeO-4-Cl-phenyl |
| 521 | 2-furanyl(cBu)CH | 2-MeO-4-Cl-phenyl |
| 522 | 3-furan(cBu)CH | 2-MeO-4-Cl-phenyl |
| 523 | 2-thienyl(cBu)CH | 2-MeO-4-Cl-phenyl |
| 524 | 3-thienyl(cBu)CH | 2-MeO-4-Cl-phenyl |
| 525 | 2-isoxazolyl(cBu)CH | 2-MeO-4-Cl-phenyl |
| 526 | 2-(5-CH₃-furanyl)(cBu)CH | 2-MeO-4-Cl-phenyl |
| 527 | 2-(4-CH₃-isoxazolyl)(cBu)CH | 2-MeO-4-Cl-phenyl |
| 528 | cBu-CH(CH₃) | 2-MeO-4-Cl-phenyl |
| 529 | 1-cBu-CH(CH₂CH₃) | 2-MeO-4-Cl-phenyl |
| 530 | 1-cBu-CH(CH₂CH₂CH₃) | 2-MeO-4-Cl-phenyl |
| 531 | 1-cBu-CH(CH₂OCH₃) | 2-MeO-4-Cl-phenyl |
| 532 | 1-cBu-CH(CH₂CH₂OCH₃) | 2-MeO-4-Cl-phenyl |
| 533 | (cPr)₂CH | 2,4-diMeO-phenyl |
| 534 | phenyl(cPr)CH | 2,4-diMeO-phenyl |
| 535 | 2-furanyl(cPr)CH | 2,4-diMeO-phenyl |
| 536 | 3-furan(cPr)CH | 2,4-diMeO-phenyl |
| 537 | 2-thienyl(cPr)CH | 2,4-diMeO-phenyl |
| 538 | 3-thienyl(cPr)CH | 2,4-diMeO-phenyl |
| 539 | 2-isoxazolyl(cPr)CH | 2,4-diMeO-phenyl |
| 540 | 2-(5-CH₃-furanyl)(cPr)CH | 2,4-diMeO-phenyl |
| 541 | 2-(4-CH₃-isoxazolyl)(cPr)CH | 2,4-diMeO-phenyl |
| 542 | cPr-CH(CH₃) | 2,4-diMeO-phenyl |
| 543 | 1-cPr-CH(CH₂CH₃) | 2,4-diMeO-phenyl |
| 544 | 1-cPr-CH(CH₂CH₂CH₃) | 2,4-diMeO-phenyl |
| 545 | 1-cPr-CH(CH₂OCH₃) | 2,4-diMeO-phenyl |
| 546 | 1-cPr-CH(CH₂CH₂OCH₃) | 2,4-diMeO-phenyl |
| 547 | (cBu)₂CH | 2,4-diMeO-phenyl |
| 548 | phenyl(cBu)CH | 2,4-diMeO-phenyl |
| 549 | 2-furanyl(cBu)CH | 2,4-diMeO-phenyl |
| 550 | 3-furan(cBu)CH | 2,4-diMeO-phenyl |
| 551 | 2-thienyl(cBu)CH | 2,4-diMeO-phenyl |
| 552 | 3-thienyl(cBu)CH | 2,4-diMeO-phenyl |
| 553 | 2-isoxazolyl(cBu)CH | 2,4-diMeO-phenyl |
| 554 | 2-(5-CH₃-furanyl)(cBu)CH | 2,4-diMeO-phenyl |
| 555 | 2-(4-CH₃-isoxazolyl)(cBu)CH | 2,4-diMeO-phenyl |
| 556 | cBu-CH(CH₃) | 2,4-diMeO-phenyl |
| 557 | 1-cBu-CH(CH₂CH₃) | 2,4-diMeO-phenyl |
| 558 | 1-cBu-CH(CH₂CH₂CH₃) | 2,4-diMeO-phenyl |
| 559 | 1-cBu-CH(CH₂OCH₃) | 2,4-diMeO-phenyl |
| 560 | 1-cBu-CH(CH₂CH₂OCH₃) | 2,4-diMeO-phenyl |
| 561 | (cPr)₂CH | 2,4-diCl-6-CH₃-phenyl |
| 562 | phenyl(cPr)CH | 2,4-diCl-6-CH₃-phenyl |
| 563 | 2-furanyl(cPr)CH | 2,4-diCl-6-CH₃-phenyl |
| 564 | 3-furan(cPr)CH | 2,4-diCl-6-CH₃-phenyl |
| 565 | 2-thienyl(cPr)CH | 2,4-diCl-6-CH₃-phenyl |
| 566 | 3-thienyl(cPr)CH | 2,4-diCl-6-CH₃-phenyl |
| 567 | 2-isoxazolyl(cPr)CH | 2,4-diCl-6-CH₃-phenyl |
| 568 | 2-(5-CH₃-furanyl)(cPr)CH | 2,4-diCl-6-CH₃-phenyl |
| 569 | 2-(4-CH₃-isoxazolyl)(cPr)CH | 2,4-diCl-6-CH₃-phenyl |
| 570 | cPr-CH(CH₃) | 2,4-diCl-6-CH₃-phenyl |
| 571 | 1-CPr-CH(CH₂CH₃) | 2,4-diCl-6-CH₃-phenyl |
| 572 | 1-cPr-CH(CH₂CH₂CH₃) | 2,4-diCl-6-CH₃-phenyl |
| 573 | 1-cPr-CH(CH₂OCH₃) | 2,4-diCl-6-CH₃-phenyl |
| 574 | 1-cPr-CH(CH₂CH₂OCH₃) | 2,4-diCl-6-CH₃-phenyl |
| 575 | (cBu)₂CH | 2,4-diCl-6-CH₃-phenyl |
| 576 | phenyl(cBu)CH | 2,4-diCl-6-CH₃-phenyl |
| 577 | 2-furanyl(cBu)CH | 2,4-diCl-6-CH₃-phenyl |
| 578 | 3-furan(cBu)CH | 2,4-diCl-6-CH₃-phenyl |
| 579 | 2-thienyl(cBu)CH | 2,4-diCl-6-CH₃-phenyl |
| 580 | 3-thienyl(cBu)CH | 2,4-diCl-6-CH₃-phenyl |
| 581 | 2-isoxazolyl(cBu)CH | 2,4-diCl-6-CH₃-phenyl |
| 582 | 2-(5-CH₃-furanyl)(cBu)CH | 2,4-diCl-6-CH₃-phenyl |
| 583 | 2-(4-CH₃-isoxazolyl)(cBu)CH | 2,4-diCl-6-CH₃-phenyl |
| 584 | cBu-CH(CH₃) | 2,4-diCl-6-CH₃-phenyl |
| 585 | 1-cBu-CH(CH₂CH₃) | 2,4-diCl-6-CH₃-phenyl |
| 586 | 1-cBu-CH(CH₂CH₂CH₃) | 2,4-diCl-6-CH₃-phenyl |
| 587 | 1-cBu-CH(CH₂OCH₃) | 2,4-diCl-6-CH₃-phenyl |
| 588 | 1-cBu-CH(CH₂CH₂OCH₃) | 2,4-diCl-6-CH₃-phenyl |
| 589 | (cPr)₂CH | 2,4-diCl-5-F-phenyl |
| 590 | phenyl(cPr)CH | 2,4-diCl-5-F-phenyl |
| 591 | 2-furanyl(cPr)CH | 2,4-diCl-5-F-phenyl |
| 592 | 3-furan(cPr)CH | 2,4-diCl-5-F-phenyl |
| 593 | 2-thienyl(cPr)CH | 2,4-diCl-5-F-phenyl |
| 594 | 3-thienyl(cPr)CH | 2,4-diCl-5-F-phenyl |
| 595 | 2-isoxazolyl(cPr)CH | 2,4-diCl-5-F-phenyl |
| 596 | 2-(5-CH₃-furanyl)(cPr)CH | 2,4-diCl-5-F-phenyl |
| 597 | 2-(4-CH₃-isoxazolyl)(cPr)CH | 2,4-diCl-5-F-phenyl |
| 598 | cPr-CH(CH₃) | 2,4-diCl-5-F-phenyl |
| 599 | 1-cPr-CH(CH₂CH₃) | 2,4-diCl-5-F-phenyl |
| 600 | 1-CPr-CH(CH₂CH₂CH₃) | 2,4-diCl-5-F-phenyl |
| 601 | 1-cPr-CH(CH₂OCH₃) | 2,4-diCl-5-F-phenyl |
| 602 | 1-cPr-CH(CH₂CH₂OCH₃) | 2,4-diCl-5-F-phenyl |
| 603 | (cBu)₂CH | 2,4-diCl-5-F-phenyl |
| 604 | phenyl(cBu)CH | 2,4-diCl-5-F-phenyl |
| 605 | 2-furanyl(cBu)CH | 2,4-diCl-5-F-phenyl |
| 606 | 3-furan(cBu)CH | 2,4-diCl-5-F-phenyl |
| 607 | 2-thienyl(cBu)CH | 2,4-diCl-5-F-phenyl |
| 608 | 3-thienyl(cBu)CH | 2,4-diCl-5-F-phenyl |
| 609 | 2-isoxazolyl(cBu)CH | 2,4-diCl-5-F-phenyl |
| 610 | 2-(5-CH₃-furanyl)(cBu)CH | 2,4-diCl-5-F-phenyl |
| 611 | 2-(4-CH₃-isoxazolyl)(cBu)CH | 2,4-diCl-5-F-phenyl |
| 612 | cBu-CH(CH₃) | 2,4-diCl-5-F-phenyl |
| 613 | 1-cBu-CH(CH₂CH₃) | 2,4-diCl-5-F-phenyl |

TABLE 3-continued

| | | |
|---|---|---|
| 614 | 1-cBu-CH(CH$_2$CH$_2$CH$_3$) | 2,4-diCl-5-F-phenyl |
| 615 | 1-cBu-CH(CH$_2$OCH$_3$) | 2,4-diCl-5-F-phenyl |
| 616 | 1-cBu-CH(CH$_2$CH$_2$OCH$_3$) | 2,4-diCl-5-F-phenyl |
| 617 | (cPr)$_2$CH | 2,4-diCl-6-MeS-phenyl |
| 618 | phenyl(cPr)CH | 2,4-diCl-6-MeS-phenyl |
| 619 | 2-furanyl(cPr)CH | 2,4-diCl-6-MeS-phenyl |
| 620 | 3-furan(cPr)CH | 2,4-diCl-6-MeS-phenyl |
| 621 | 2-thienyl(cPr)CH | 2,4-diCl-6-MeS-phenyl |
| 622 | 3-thienyl(cPr)CH | 2,4-diCl-6-MeS-phenyl |
| 623 | 2-isoxazolyl(cPr)CH | 2,4-diCl-6-MeS-phenyl |
| 624 | 2-(5-CH$_3$-furanyl)(cPr)CH | 2,4-diCl-6-MeS-phenyl |
| 625 | 2-(4-CH$_3$-isoxazolyl)(cPr)CH | 2,4-diCl-6-MeS-phenyl |
| 626 | cPr-CH(CH$_3$) | 2,4-diCl-6-MeS-phenyl |
| 627 | 1-cPr-CH(CH$_2$CH$_3$) | 2,4-diCl-6-MeS-phenyl |
| 628 | 1-cPr-CH(CH$_2$CH$_2$CH$_3$) | 2,4-diCl-6-MeS-phenyl |
| 629 | 1-cPr-CH(CH$_2$OCH$_3$) | 2,4-diCl-6-MeS-phenyl |
| 630 | 1-cPr-CH(CH$_2$CH$_2$OCH$_3$) | 2,4-diCl-6-MeS-phenyl |
| 631 | (cBu)$_2$CH | 2,4-diCl-6-MeS-phenyl |
| 632 | phenyl(cBu)CH | 2,4-diCl-6-MeS-phenyl |
| 633 | 2-furanyl(cBu)CH | 2,4-diCl-6-MeS-phenyl |
| 634 | 3-furan(cBu)CH | 2,4-diCl-6-MeS-phenyl |
| 635 | 2-thienyl(cBu)CH | 2,4-diCl-6-MeS-phenyl |
| 636 | 3-thienyl(cBu)CH | 2,4-diCl-6-MeS-phenyl |
| 637 | 2-isoxazolyl(cBu)CH | 2,4-diCl-6-MeS-phenyl |
| 638 | 2-(5-CH$_3$-furanyl)(cBu)CH | 2,4-diCl-6-MeS-phenyl |
| 639 | 2-(4-CH$_3$-isoxazolyl)(cBu)CH | 2,4-diCl-6-MeS-phenyl |
| 640 | cBu-CH(CH$_3$) | 2,4-diCl-6-MeS-phenyl |
| 641 | 1-cBu-CH(CH$_2$CH$_3$) | 2,4-diCl-6-MeS-phenyl |
| 642 | 1-cBu-CH(CH$_2$CH$_2$CH$_3$) | 2,4-diCl-6-MeS-phenyl |
| 643 | 1-cBu-CH(CH$_2$OCH$_3$) | 2,4-diCl-6-MeS-phenyl |
| 644 | 1-cBu-CH(CH$_2$CH$_2$OCH$_3$) | 2,4-diCl-6-MeS-phenyl |
| 645 | (cPr)$_2$CH | 2,4-diCl-6-MeO-phenyl |
| 646 | phenyl(cPr)CH | 2,4-diCl-6-MeO-phenyl |
| 647 | 2-furanyl(cPr)CH | 2,4-diCl-6-MeO-phenyl |
| 648 | 3-furan(cPr)CH | 2,4-diCl-6-MeO-phenyl |
| 649 | 2-thienyl(cPr)CH | 2,4-diCl-6-MeO-phenyl |
| 650 | 3-thienyl(cPr)CH | 2,4-diCl-6-MeO-phenyl |
| 651 | 2-isoxazolyl(cPr)CH | 2,4-diCl-6-MeO-phenyl |
| 652 | 2-(5-CH$_3$-furanyl)(cPr)CH | 2,4-diCl-6-MeO-phenyl |
| 653 | 2-(4-CH$_3$-isoxazolyl)(cPr)CH | 2,4-diCl-6-MeO-phenyl |
| 654 | cPr-CH(CH$_3$) | 2,4-diCl-6-MeO-phenyl |
| 655 | 1-cPr-CH(CH$_2$CH$_3$) | 2,4-diCl-6-MeO-phenyl |
| 656 | 1-cPr-CH(CH$_2$CH$_2$CH$_3$) | 2,4-diCl-6-MeO-phenyl |
| 657 | 1-cPr-CH(CH$_2$OCH$_3$) | 2,4-diCl-6-MeO-phenyl |
| 658 | 1-cPr-CH(CH$_2$CH$_2$OCH$_3$) | 2,4-diCl-6-MeO-phenyl |
| 659 | (cBu)$_2$CH | 2,4-diCl-6-MeO-phenyl |
| 660 | phenyl(cBu)CH | 2,4-diCl-6-MeO-phenyl |
| 661 | 2-furanyl(cBu)CH | 2,4-diCl-6-MeO-phenyl |
| 662 | 3-furan(cBu)CH | 2,4-diCl-6-MeO-phenyl |
| 663 | 2-thienyl(cBu)CH | 2,4-diCl-6-MeO-phenyl |
| 664 | 3-thienyl(cBu)CH | 2,4-diCl-6-MeO-phenyl |
| 665 | 2-isaxolyl(cBu)CH | 2,4-diCl-6-MeO-phenyl |
| 666 | 2-(5-CH$_3$-furanyl)(cBu)CH | 2,4-diCl-6-MeO-phenyl |
| 667 | 2-(4-CH$_3$-isoxazolyl)(cBu)CH | 2,4-diCl-6-MeO-phenyl |
| 668 | cBu-CH(CH$_3$) | 2,4-diCl-6-MeO-phenyl |
| 669 | 1-cBu-CH(CH$_2$CH$_3$) | 2,4-diCl-6-MeO-phenyl |
| 670 | 1-cBu-CH(CH$_2$CH$_2$CH$_3$) | 2,4-diCl-6-MeO-phenyl |
| 671 | 1-cBu-CH(CH$_2$OCH$_3$) | 2,4-diCl-6-MeO-phenyl |
| 672 | 1-cBu-CH(CH$_2$CH$_2$OCH$_3$) | 2,4-diCl-6-MeO-phenyl |
| 673 | (cPr)$_2$CH | 2,5-diCl-4-MeO-phenyl |
| 674 | phenyl(cPr)CH | 2,5-diCl-4-MeO-phenyl |
| 675 | 2-furanyl(cPr)CH | 2,5-diCl-4-MeO-phenyl |
| 676 | 3-furan(cPr)CH | 2,5-diCl-4-MeO-phenyl |
| 677 | 2-thienyl(cPr)CH | 2,5-diCl-4-MeO-phenyl |
| 678 | 3-thienyl(cPr)CH | 2,5-diCl-4-MeO-phenyl |
| 679 | 2-isoxazolyl(cPr)CH | 2,5-diCl-4-MeO-phenyl |
| 680 | 2-(5-CH$_3$-furanyl)(cPr)CH | 2,5-diCl-4-MeO-phenyl |
| 681 | 2-(4-CH$_3$-isoxazolyl)(cPr)CH | 2,5-diCl-4-MeO-phenyl |
| 682 | cPr-CH(CH$_3$) | 2,5-diCl-4-MeO-phenyl |
| 683 | 1-cPr-CH(CH$_2$CH$_3$) | 2,5-diCl-4-MeO-phenyl |
| 684 | 1-cPr-CH(CH$_2$CH$_2$CH$_3$) | 2,5-diCl-4-MeO-phenyl |
| 685 | 1-cPr-CH(CH$_2$OCH$_3$) | 2,5-diCl-4-MeO-phenyl |
| 686 | 1-cPr-CH(CH$_2$CH$_2$OCH$_3$) | 2,5-diCl-4-MeO-phenyl |
| 687 | (cBu)$_2$CH | 2,5-diCl-4-MeO-phenyl |
| 688 | phenyl(cBu)CH | 2,5-diCl-4-MeO-phenyl |
| 689 | 2-furanyl(cBu)CH | 2,5-diCl-4-MeO-phenyl |
| 690 | 3-furan(cBu)CH | 2,5-diCl-4-MeO-phenyl |
| 691 | 2-thienyl(cBu)CH | 2,5-diCl-4-MeO-phenyl |
| 692 | 3-thienyl(cBu)CH | 2,5-diCl-4-MeO-phenyl |
| 693 | 2-isoxazolyl(cBu)CH | 2,5-diCl-4-MeO-phenyl |
| 694 | 2-(5-CH$_3$-furanyl)(cBu)CH | 2,5-diCl-4-MeO-phenyl |
| 695 | 2-(4-CH$_3$-isoxazolyl)(cBu)CH | 2,5-diCl-4-MeO-phenyl |
| 696 | cBu-CH(CH$_3$) | 2,5-diCl-4-MeO-phenyl |
| 697 | 1-cBu-CH(CH$_2$CH$_3$) | 2,5-diCl-4-MeO-phenyl |
| 698 | 1-cBu-CH(CH$_2$CH$_2$CH$_3$) | 2,5-diCl-4-MeO-phenyl |
| 699 | 1-cBu-CH(CH$_2$OCH$_3$) | 2,5-diCl-4-MeO-phenyl |
| 700 | 1-cBu-CH(CH$_2$CH$_2$OCH$_3$) | 2,5-diCl-4-MeO-phenyl |
| 701 | (cPr)$_2$CH | 2,4,6-triCl-phenyl |
| 702 | phenyl(cPr)CH | 2,4,6-triCl-phenyl |
| 703 | 2-furanyl(cPr)CH | 2,4,6-triCl-phenyl |
| 704 | 3-furan(cPr)CH | 2,4,6-triCl-phenyl |
| 705 | 2-thienyl(cPr)CH | 2,4,6-triCl-phenyl |
| 706 | 3-thienyl(cPr)CH | 2,4,6-triCl-phenyl |
| 707 | 2-isoxazolyl(cPr)CH | 2,4,6-triCl-phenyl |
| 708 | 2-(5-CH$_3$-furanyl)(cPr)CH | 2,4,6-triCl-phenyl |
| 709 | 2-(4-CH$_3$-isoxazolyl)(cPr)CH | 2,4,6-triCl-phenyl |
| 710 | cPr-CH(CH$_3$) | 2,4,6-triCl-phenyl |
| 711 | 1-cPr-CH(CH$_2$CH$_3$) | 2,4,6-triCl-phenyl |
| 712 | 1-cPr-CH(CH$_2$CH$_2$CH$_3$) | 2,4,6-triCl-phenyl |
| 713 | i-cPr-CH(CH$_2$OCH$_3$) | 2,4,6-triCl-phenyl |
| 714 | 1-cPr-CH(CH$_2$CH$_2$OCH$_3$) | 2,4,6-triCl-phenyl |
| 715 | (cBu)$_2$CH | 2,4,6-triCl-phenyl |
| 716 | phenyl(cBu)CH | 2,4,6-triCl-phenyl |
| 717 | 2-furanyl(cBu)CH | 2,4,6-triCl-phenyl |
| 718 | 3-furan(cBu)CH | 2,4,6-triCl-phenyl |
| 719 | 2-thienyl(cBu)CH | 2,4,6-triCl-phenyl |
| 720 | 3-thienyl(cBu)CH | 2,4,6-triCl-phenyl |
| 721 | 2-isoxazolyl(cBu)CH | 2,4,6-triCl-phenyl |
| 722 | 2-(5-CH$_3$-furanyl)(cBu)CH | 2,4,6-triCl-phenyl |
| 723 | 2-(4-CH$_3$-isoxazolyl)(cBu)CH | 2,4,6-triCl-phenyl |
| 724 | cBu-CH(CH$_3$) | 2,4,6-triCl-phenyl |
| 725 | 1-cBu-CH(CH$_2$CH$_3$) | 2,4,6-triCl-phenyl |
| 726 | 1-cBu-CH(CH$_2$CH$_2$CH$_3$) | 2,4,6-triCl-phenyl |
| 727 | 1-cBu-CH(CH$_2$OCH$_3$) | 2,4,6-triCl-phenyl |
| 728 | 1-cBu-CH(CH$_2$CH$_2$OCH$_3$) | 2,4,6-triCl-phenyl |
| 729 | (cPr)$_2$CH | 2-Cl-4-CH$_3$-5-F-phenyl |
| 730 | phenyl(cPr)CH | 2-Cl-4-CH$_3$-5-F-phenyl |
| 731 | 2-furanyl(cPr)CH | 2-Cl-4-CH$_3$-5-F-phenyl |
| 732 | 3-furan(cPr)CH | 2-Cl-4-CH$_3$-5-F-phenyl |
| 733 | 2-thienyl(cPr)CH | 2-Cl-4-CH$_3$-5-F-phenyl |
| 734 | 3-thlenyl(cPr)CH | 2-Cl-4-CH$_3$-5-F-phenyl |
| 735 | 2-isoxazolyl(cPr)CH | 2-Cl-4-CH$_3$-5-F-phenyl |
| 736 | 2-(5-CH$_3$-furanyl)(cPr)CH | 2-Cl-4-CH$_3$-5-F-phenyl |
| 737 | 2-(4-CH$_3$-isoxazolyl)(cPr)CH | 2-Cl-4-CH$_3$-5-F-phenyl |
| 738 | cPr-CH(CH$_3$) | 2-Cl-4-CH$_3$-5-F-phenyl |
| 739 | 1-cPr-CH(CH$_2$CH$_3$) | 2-Cl-4-CH$_3$-5-F-phenyl |
| 740 | 1-cPr-CH(CH$_2$CH$_2$CH$_3$) | 2-Cl-4-CH$_3$-5-F-phenyl |
| 741 | 1-cPr-CH(CH$_2$OCH$_3$) | 2-Cl-4-CH$_3$-5-F-phenyl |
| 742 | 1-cPr-CH(CH$_2$CH$_2$OCH$_3$) | 2-Cl-4-CH$_3$-5-F-phenyl |
| 743 | (cBu)$_2$CH | 2-Cl-4-CH$_3$-5-F-phenyl |
| 744 | phenyl(cBu)CH | 2-Cl-4-CH$_3$-5-F-phenyl |
| 745 | 2-furanyl(cBu)CH | 2-Cl-4-CH$_3$-5-F-phenyl |
| 746 | 3-furan(cBu)CH | 2-Cl-4-CH$_3$-5-F-phenyl |
| 747 | 2-thienyl(cBu)CH | 2-Cl-4-CH$_3$-5-F-phenyl |
| 748 | 3-thienyl(cBu)CH | 2-Cl-4-CH$_3$-5-F-phenyl |
| 749 | 2-isoxazolyl(cBu)CH | 2-Cl-4-CH$_3$-5-F-phenyl |
| 750 | 2-(5-CH$_3$-furanyl)(cBu)CH | 2-Cl-4-CH$_3$-5-F-phenyl |
| 751 | 2-(4-CH$_3$-isoxazolyl)(cBu)CH | 2-Cl-4-CH$_3$-5-F-phenyl |
| 752 | cBu-CH(CH$_3$) | 2-Cl-4-CH$_3$-5-F-phenyl |
| 753 | 1-cBu-CH(CH$_2$CH$_3$) | 2-Cl-4-CH$_3$-5-F-phenyl |
| 754 | 1-cBu-CH(CH$_2$CH$_2$CH$_3$) | 2-Cl-4-CH$_3$-5-F-phenyl |
| 755 | 1-cBu-CH(CH$_2$OCH$_3$) | 2-Cl-4-CH$_3$-5-F-phenyl |
| 756 | 1-cBu-CH(CH$_2$CH$_2$OCH$_3$) | 2-Cl-4-CH$_3$-5-F-phenyl |
| 757 | (cPr)$_2$CH | 2-Cl-4-MeO-5-CH$_3$-phenyl |
| 758 | phenyl(cPr)CH | 2-Cl-4-MeO-5-CH$_3$-phenyl |
| 759 | 2-furanyl(cPr)CH | 2-Cl-4-MeO-5-CH$_3$-phenyl |
| 760 | 3-furan(cPr)CH | 2-Cl-4-MeO-5-CH$_3$-phenyl |
| 761 | 2-thienyl(cPr)CH | 2-Cl-4-MeO-5-CH$_3$-phenyl |
| 762 | 3-thienyl(cPr)CH | 2-Cl-4-MeO-5-CH$_3$-phenyl |
| 763 | 2-isoxazolyl(cPr)CH | 2-Cl-4-MeO-5-CH$_3$-phenyl |
| 764 | 2-(5-CH$_3$-furanyl)(cPr)CH | 2-Cl-4-MeO-5-CH$_3$-phenyl |
| 765 | 2-(4-CH$_3$-isoxazolyl)(cPr)CH | 2-Cl-4-MeO-5-CH$_3$-phenyl |
| 766 | cPr-CH(CH$_3$) | 2-Cl-4-MeO-5-CH$_3$-phenyl |
| 767 | 1-cPr-CH(CH$_2$CH$_3$) | 2-Cl-4-MeO-5-CH$_3$-phenyl |
| 768 | 1-cPr-CH(CH$_2$CH$_2$CH$_3$) | 2-Cl-4-MeO-5-CH$_3$-phenyl |
| 769 | 1-cPr-CH(CH$_2$OCH$_3$) | 2-Cl-4-MeO-5-CH$_3$-phenyl |
| 770 | 1-cPr-CH(CH$_2$CH$_2$OCH$_3$) | 2-Cl-4-MeO-5-CH$_3$-phenyl |
| 771 | (cBu)$_2$CH | 2-Cl-4-MeO-5-CH$_3$-phenyl |

TABLE 3-continued

| | | |
|---|---|---|
| 772 | phenyl(cBu)CH | 2-Cl-4-MeO-5-CH$_3$-phenyl |
| 773 | 2-furanyl(cBu)CH | 2-Cl-4-MeO-5-CH$_3$-phenyl |
| 774 | 3-furan(cBu)CH | 2-Cl-4-MeO-5-CH$_3$-phenyl |
| 775 | 2-thienyl(cBu)CH | 2-Cl-4-MeO-5-CH$_3$-phenyl |
| 776 | 3-thienyl(cBu)CH | 2-Cl-4-MeO-5-CH$_3$-phenyl |
| 777 | 2-isoxazolyl(cBu)CH | 2-Cl-4-MeO-5-CH$_3$-phenyl |
| 778 | 2-(5-CH$_3$-furanyl)(cBu)CH | 2-Cl-4-MeO-5-CH$_3$-phenyl |
| 779 | 2-(4-CH$_3$-isoxazolyl)(cBu)CH | 2-Cl-4-MeO-5-CH$_3$-phenyl |
| 780 | cBu-CH(CH$_3$) | 2-Cl-4-MeO-5-CH$_3$-phenyl |
| 781 | 1-cBu-CH(CH$_2$CH$_3$) | 2-Cl-4-MeO-5-CH$_3$-phenyl |
| 782 | 1-cBu-CH(CH$_2$CH$_2$CH$_3$) | 2-Cl-4-MeO-5-CH$_3$-phenyl |
| 783 | 1-cBu-CH(CH$_2$OCH$_3$) | 2-Cl-4-MeO-5-CH$_3$-phenyl |
| 784 | 1-cBu-CH(CH$_2$CH$_2$OCH$_3$) | 2-Cl-4-MeO-5-CH$_3$-phenyl |
| 785 | (cPr)$_2$CH | 2-Cl-4-MeO-5-F-phenyl |
| 786 | phenyl(cPr)CH | 2-Cl-4-MeO-5-F-phenyl |
| 787 | 2-furanyl(cPr)CH | 2-Cl-4-MeO-5-F-phenyl |
| 788 | 3-furan(cPr)CH | 2-Cl-4-MeO-5-F-phenyl |
| 789 | 2-thienyl(cPr)CH | 2-Cl-4-MeO-5-F-phenyl |
| 790 | 3-thienyl(cPr)CH | 2-Cl-4-MeO-5-F-phenyl |
| 791 | 2-isoxazolyl(cPr)CH | 2-Cl-4-MeO-5-F-phenyl |
| 792 | 2-(5-CH$_3$-furanyl)(cPr)CH | 2-Cl-4-MeO-5-F-phenyl |
| 793 | 2-(4-CH$_3$-isoxazolyl)(cPr)CH | 2-Cl-4-MeO-5-F-phenyl |
| 794 | cPr-CH(CH$_3$) | 2-Cl-4-MeO-5-F-phenyl |
| 795 | 1-cPr-CH(CH$_2$CH$_3$) | 2-Cl-4-MeO-5-F-phenyl |
| 796 | 1-cPr-CH(CH$_2$CH$_2$CH$_3$) | 2-Cl-4-MeO-5-F-phenyl |
| 797 | 1-cPr-CH(CH$_2$OCH$_3$) | 2-Cl-4-MeO-5-F-phenyl |
| 798 | 1-cPr-CH(CH$_2$CH$_2$OCH$_3$) | 2-Cl-4-MeO-5-F-phenyl |
| 799 | (cBu)$_2$CH | 2-Cl-4-MeO-5-F-phenyl |
| 800 | phenyl(cBu)CH | 2-Cl-4-MeO-5-F-phenyl |
| 801 | 2-furanyl(cBu)CH | 2-Cl-4-MeO-5-F-phenyl |
| 802 | 3-furan(cBu)CH | 2-Cl-4-MeO-5-F-phenyl |
| 803 | 2-thienyl(cBu)CH | 2-Cl-4-MeO-5-F-phenyl |
| 804 | 3-thienyl(cBu)CH | 2-Cl-4-MeO-5-F-phenyl |
| 805 | 2-isoxazolyl(cBu)CH | 2-Cl-4-MeO-5-F-phenyl |
| 806 | 2-(5-CH$_3$-furanyl)(cBu)CH | 2-Cl-4-MeO-5-F-phenyl |
| 807 | 2-(4-CH$_3$-isoxazolyl)(cBu)CH | 2-Cl-4-MeO-5-F-phenyl |
| 808 | cBu-CH(CH$_3$) | 2-Cl-4-MeO-5-F-phenyl |
| 809 | 1-cBu-CH(CH$_2$CH$_3$) | 2-Cl-4-MeO-5-F-phenyl |
| 810 | 1-cBu-CH(CH$_2$CH$_2$CH$_3$) | 2-Cl-4-MeO-5-F-phenyl |
| 811 | 1-cBu-CH(CH$_2$OCH$_3$) | 2-Cl-4-MeO-5-F-phenyl |
| 812 | 1-cBu-CH(CH$_2$CH$_2$OCH$_3$) | 2-Cl-4-MeO-5-F-phenyl |
| 813 | (cPr)$_2$CH | 2-CH$_3$-4-MeO-5-Cl-phenyl |
| 814 | phenyl(cPr)CH | 2-CH$_3$-4-MeO-5-Cl-phenyl |
| 815 | 2-furanyl(cPr)CH | 2-CH$_3$-4-MeO-5-Cl-phenyl |
| 816 | 3-furan(cPr)CH | 2-CH$_3$-4-MeO-5-Cl-phenyl |
| 817 | 2-thienyl(cPr)CH | 2-CH$_3$-4-MeO-5-Cl-phenyl |
| 818 | 3-thienyl(cPr)CH | 2-CH$_3$-4-MeO-5-Cl-phenyl |
| 819 | 2-isoxazolyl(cPr)CH | 2-CH$_3$-4-MeO-5-Cl-phenyl |
| 820 | 2-(5-CH$_3$-furanyl)(cPr)CH | 2-CH$_3$-4-MeO-5-Cl-phenyl |
| 821 | 2-(4-CH$_3$-isoxazolyl)(cPr)CH | 2-CH$_3$-4-MeO-5-Cl-phenyl |
| 822 | cPr-CH(CH$_3$) | 2-CH$_3$-4-MeO-5-Cl-phenyl |
| 823 | 1-cPr-CH(CH$_2$CH$_3$) | 2-CH$_3$-4-MeO-5-Cl-phenyl |
| 824 | 1-cPr-CH(CH$_2$CH$_2$CH$_3$) | 2-CH$_3$-4-MeO-5-Cl-phenyl |
| 825 | 1-cPr-CH(CH$_2$OCH$_3$) | 2-CH$_3$-4-MeO-5-Cl-phenyl |
| 826 | 1-cPr-CH(CH$_2$CH$_2$OCH$_3$) | 2-CH$_3$-4-MeO-5-Cl-phenyl |
| 827 | (cBu)$_2$CH | 2-CH$_3$-4-MeO-5-Cl-phenyl |
| 828 | phenyl(cBu)CH | 2-CH$_3$-4-MeO-5-Cl-phenyl |
| 829 | 2-furanyl(cBu)CH | 2-CH$_3$-4-MeO-5-Cl-phenyl |
| 830 | 3-furan(cBu)CH | 2-CH$_3$-4-MeO-5-Cl-phenyl |
| 831 | 2-thienyl(cBu)CH | 2-CH$_3$-4-MeO-5-Cl-phenyl |
| 832 | 3-thienyl(cBu)CH | 2-CH$_3$-4-MeO-5-Cl-phenyl |
| 833 | 2-isoxazolyl(cBu)CH | 2-CH$_3$-4-MeO-5-Cl-phenyl |
| 834 | 2-(5-CH$_3$-furanyl)(cBu)CH | 2-CH$_3$-4-MeO-5-Cl-phenyl |
| 835 | 2-(4-CH$_3$-isoxazolyl)(cBu)CH | 2-CH$_3$-4-MeO-5-Cl-phenyl |
| 836 | cBu-CH(CH$_3$) | 2-CH$_3$-4-MeO-5-Cl-phenyl |
| 837 | 1-cBu-CH(CH$_2$CH$_3$) | 2-CH$_3$-4-MeO-5-Cl-phenyl |
| 838 | 1-cBu-CH(CH$_2$CH$_2$CH$_3$) | 2-CH$_3$-4-MeO-5-Cl-phenyl |
| 839 | 1-cBu-CH(CH$_2$OCH$_3$) | 2-CH$_3$-4-MeO-5-Cl-phenyl |
| 840 | 1-cBu-CH(CH$_2$CH$_2$OCH$_3$) | 2-CH$_3$-4-MeO-5-Cl-phenyl |
| 841 | (cPr)$_2$CH | 2,5-diCH$_3$-4-MeO-phenyl |
| 842 | phenyl(cPr)CH | 2,5-diCH$_3$-4-MeO-phenyl |
| 843 | 2-furanyl(cPr)CH | 2,5-diCH$_3$-4-MeO-phenyl |
| 844 | 3-furan(cPr)CH | 2,5-diCH$_3$-4-MeO-phenyl |
| 845 | 2-thienyl(cPr)CH | 2,5-diCH$_3$-4-MeO-phenyl |
| 846 | 3-thienyl(cPr)CH | 2,5-diCH$_3$-4-MeO-phenyl |
| 847 | 2-isoxazolyl(cPr)CH | 2,5-diCH$_3$-4-MeO-phenyl |
| 848 | 2-(5-CH$_3$-furanyl)(cPr)CH | 2,5-diCH$_3$-4-MeO-phenyl |
| 849 | 2-(4-CH$_3$-isoxazolyl)(cPr)CH | 2,5-diCH$_3$-4-MeO-phenyl |
| 850 | cPr-CH(CH$_3$) | 2,5-diCH$_3$-4-MeO-phenyl |
| 851 | 1-cPr-CH(CH$_2$CH$_3$) | 2,5-diCH$_3$-4-MeO-phenyl |
| 852 | 1-cPr-CH(CH$_2$CH$_2$CH$_3$) | 2,5-diCH$_3$-4-MeO-phenyl |
| 853 | 1-cPr-CH(CH$_2$OCH$_3$) | 2,5-diCH$_3$-4-MeO-phenyl |
| 854 | 1-cPr-CH(CH$_2$CH$_2$OCH$_3$) | 2,5-diCH$_3$-4-MeO-phenyl |
| 855 | (cBu)$_2$CH | 2,5-diCH$_3$-4-MeO-phenyl |
| 856 | phenyl(cBu)CH | 2,5-diCH$_3$-4-MeO-phenyl |
| 857 | 2-furanyl(cBu)CH | 2,5-diCH$_3$-4-MeO-phenyl |
| 858 | 3-furan(cBu)CH | 2,5-diCH$_3$-4-MeO-phenyl |
| 859 | 2-thienyl(cBu)CH | 2,5-diCH$_3$-4-MeO-phenyl |
| 860 | 3-thienyl(cBu)CH | 2,5-diCH$_3$-4-MeO-phenyl |
| 861 | 2-isdxazolyl(cBu)CH | 2,5-diCH$_3$-4-MeO-phenyl |
| 862 | 2-(5-CH$_3$-furanyl)(cBu)CH | 2,5-diCH$_3$-4-MeO-phenyl |
| 863 | 2-(4-CH$_3$-isoxazolyl)(cBu)CH | 2,5-diCH$_3$-4-MeO-phenyl |
| 864 | cBu-CH(CH$_3$) | 2,5-diCH$_3$-4-MeO-phenyl |
| 865 | 1-cBu-CH(CH$_2$CH$_3$) | 2,5-diCH$_3$-4-MeO-phenyl |
| 866 | 1-cBu-CH(CH$_2$CH$_2$CH$_3$) | 2,5-diCH$_3$-4-MeO-phenyl |
| 867 | 1-cBu-CH(CH$_2$OCH$_3$) | 2,5-diCH$_3$-4-MeO-phenyl |
| 868 | 1-cBu-CH(CH$_2$CH$_2$OCH$_3$) | 2,5-diCH$_3$-4-MeO-phenyl |
| 869 | (cPr)$_2$CH | 2-CH$_3$-4-MeO-5-F-phenyl |
| 870 | phenyl(cPr)CH | 2-CH$_3$-4-MeO-5-F-phenyl |
| 871 | 2-furanyl(cPr)CH | 2-CH$_3$-4-MeO-5-F-phenyl |
| 872 | 3-furan(cPr)CH | 2-CH$_3$-4-MeO-5-F-phenyl |
| 873 | 2-thienyl(cPr)CH | 2-CH$_3$-4-MeO-5-F-phenyl |
| 874 | 3-thienyl(cPr)CH | 2-CH$_3$-4-MeO-5-F-phenyl |
| 875 | 2-isoxazolyl(cPr)CH | 2-CH$_3$-4-MeO-5-F-phenyl |
| 876 | 2-(5-CH$_3$-furanyl)(cPr)CH | 2-CH$_3$-4-MeO-5-F-phenyl |
| 877 | 2-(4-CH$_3$-isoxazolyl)(cPr)CH | 2-CH$_3$-4-MeO-5-F-phenyl |
| 878 | cPr-CH(CH$_3$) | 2-CH$_3$-4-MeO-5-F-phenyl |
| 879 | 1-cPr-CH(CH$_2$CH$_3$) | 2-CH$_3$-4-MeO-5-F-phenyl |
| 880 | 1-cPr-CH(CH$_2$CH$_2$CH$_3$) | 2-CH$_3$-4-MeO-5-F-phenyl |
| 881 | 1-cPr-CH(CH$_2$OCH$_3$) | 2-CH$_3$-4-MeO-5-F-phenyl |
| 882 | l-cPr-CH(CH$_2$CH$_2$OCH$_3$) | 2-CH$_3$-4-MeO-5-F-phenyl |
| 883 | (cBu)$_2$CH | 2-CH$_3$-4-MeO-5-F-phenyl |
| 884 | phenyl(cBu)CH | 2-CH$_3$-4-MeO-5-F-phenyl |
| 885 | 2-furanyl(cBu)CH | 2-CH$_3$-4-MeO-5-F-phenyl |
| 886 | 3-furan(cBu)CH | 2-CH$_3$-4-MeO-5-F-phenyl |
| 887 | 2-thienyl(cBu)CH | 2-CH$_3$-4-MeO-5-F-phenyl |
| 888 | 3-thienyl(cBu)CH | 2-CH$_3$-4-MeO-5-F-phenyl |
| 889 | 2-isoxazolyl(aBu)CH | 2-CH$_3$-4-MeO-5-F-phenyl |
| 890 | 2-(5-CH$_3$-furanyl)(cBu)CH | 2-CH$_3$-4-MeO-5-F-phenyl |
| 891 | 2-(4-CH$_3$-isoxazolyl)(cBu)CH | 2-CH$_3$-4-MeO-5-F-phenyl |
| 892 | cBu-CH(CH$_3$) | 2-CH$_3$-4-MeO-5-F-phenyl |
| 893 | 1-cBu-CH(CH$_2$CH$_3$) | 2-CH$_3$-4-MeO-5-F-phenyl |
| 894 | 1-cBu-CH(CH$_2$CH$_2$CH$_3$) | 2-CH$_3$-4-MeO-5-F-phenyl |
| 895 | 1-cBu-CH(CH$_2$OCH$_3$) | 2-CH$_3$-4-MeO-5-F-phenyl |
| 896 | 1-cBu-CH(CH$_2$CH$_2$OCH$_3$) | 2-CH$_3$-4-MeO-5-F-phenyl |
| 897 | (cPr)$_2$CH | 2,4,6-triCH$_3$-phenyl |
| 898 | phenyl(cPr)CH | 2,4,6-triCH$_3$-phenyl |
| 899 | 2-furanyl(cPr)CH | 2,4,6-triCH$_3$-phenyl |
| 900 | 3-furan(cPr)CH | 2,4,6-triCH$_3$-phenyl |
| 901 | 2-thienyl(cPr)CH | 2,4,6-triCH$_3$-phenyl |
| 902 | 3-thienyl(cPr)CH | 2,4,6-triCH$_3$-phenyl |
| 903 | 2-isoxazolyl(cPr)CH | 2,4,6-triCH$_3$-phenyl |
| 904 | 2-(5-CH$_3$-furanyl)(cPr)CH | 2,4,6-triCH$_3$-phenyl |
| 905 | 2-(4-CH$_3$-isoxazolyl)(cPr)CH | 2,4,6-triCH$_3$-phenyl |
| 906 | cPr-CH(CH$_3$) | 2,4,6-triCH$_3$-phenyl |
| 907 | 1-cPr-CH(CH$_2$CH$_3$) | 2,4,6-triCH$_3$-phenyl |
| 908 | l-cPr-CH(CH$_2$CH$_2$CH$_3$) | 2,4,6-triCH$_3$-phenyl |
| 909 | l-cPr-CH(CH$_2$OCH$_3$) | 2,4,6-triCH$_3$-phenyl |
| 910 | l-cPr-CH(CH$_2$CH$_2$OCH$_3$) | 2,4,6-triCH$_3$-phenyl |
| 911 | (cBu)$_2$CH | 2,4,6-triCH$_3$-phenyl |
| 912 | phenyl(cBu)CH | 2,4,6-triCH$_3$-phenyl |
| 913 | 2-furanyl(cBu)CH | 2,4,6-triCH$_3$-phenyl |
| 914 | 3-furan(cBu)CH | 2,4,6-triCH$_3$-phenyl |
| 915 | 2-thienyl(cBu)CH | 2,4,6-triCH$_3$-phenyl |
| 916 | 3-thienyl(cBu)CH | 2,4,6-triCH$_3$-phenyl |
| 917 | 2-isoxazolyl(cBu)CH | 2,4,6-triCH$_3$-phenyl |
| 918 | 2-(5-CH$_3$-furanyl)(cBu)CH | 2,4,6-triCH$_3$-phenyl |
| 919 | 2-(4-CH$_3$-isoxazolyl)(cBu)CH | 2,4,6-triCH$_3$-phenyl |
| 920 | cBu-CH(CH$_3$) | 2,4,6-triCH$_3$-phenyl |
| 921 | 1-cBu-CH(CH$_2$CH$_3$) | 2,4,6-triCH$_3$-phenyl |
| 922 | 1-cBu-CH(CH$_2$CH$_2$CH$_3$) | 2,4,6-triCH$_3$-phenyl |
| 923 | 1-cBu-CH(CH$_2$OCH$_3$) | 2,4,6-triCH$_3$-phenyl |
| 924 | 1-cBu-CH(CH$_2$CH$_2$OCH$_3$) | 2,4,6-triCH$_3$-phenyl |
| 925 | (cPr)$_2$CH | 2,6-diMeO-pyrid-3-yl |
| 926 | phenyl(cPr)CH | 2,6-diMeO-pyrid-3-yl |
| 927 | 2-furanyl(cPr)CH | 2,6-diMeO-pyrid-3-yl |
| 928 | 3-furan(cPr)CH | 2,6-diMeO-pyrid-3-yl |
| 929 | 2-thienyl(cPr)CH | 2,6-diMeO-pyrid-3-yl |

TABLE 3-continued

| | | |
|---|---|---|
| 930 | 3-thienyl(cPr)CH | 2,6-diMeO-pyrid-3-yl |
| 931 | 2-isoxazolyl(cPr)CH | 2,6-diMeO-pyrid-3-yl |
| 932 | 2-(5-CH$_3$-furanyl)(cPr)CH | 2,6-diMeO-pyrid-3-yl |
| 933 | 2-(4-CH$_3$-isoxazolyl)(cPr)CH | 2,6-diMeO-pyrid-3-yl |
| 934 | cPr-CH(CH$_3$) | 2,6-diMeO-pyrid-3-yl |
| 935 | 1-cPr-CH(CH$_2$CH$_3$) | 2,6-diMeO-pyrid-3-yl |
| 936 | 1-cPr-CH(CH$_2$CH$_2$CH$_3$) | 2,6-diMeO-pyrid-3-yl |
| 937 | 1-cPr-CH(CH$_2$OCH$_3$) | 2,6-diMeO-pyrid-3-yl |
| 938 | 1-cPr-CH(CH$_2$CH$_2$OCH$_3$) | 2,6-diMeO-pyrid-3-yl |
| 939 | (cBu)$_2$CH | 2,6-diMeO-pyrid-3-yl |
| 940 | phenyl(cBu)CH | 2,6-diMeO-pyrid-3-yl |
| 941 | 2-furanyl(cBu)CH | 2,6-diMeO-pyrid-3-yl |
| 942 | 3-furan(cBu)CH | 2,6-diMeO-pyrid-3-yl |
| 943 | 2-thienyl(cBu)CH | 2,6-diMeO-pyrid-3-yl |
| 944 | 3-thienyl(cBu)CH | 2,6-diMeO-pyrid-3-yl |
| 945 | 2-isoxazolyl(cBu)CH | 2,6-diMeO-pyrid-3-yl |
| 946 | 2-(5-CH$_3$-furanyl)(cBu)CH | 2,6-diMeO-pyrid-3-yl |
| 947 | 2-(4-CH$_3$-isoxazolyl)(cBu)CH | 2,6-diMeO-pyrid-3-yl |
| 948 | cBu-CH(CH$_3$) | 2,6-diMeO-pyrid-3-yl |
| 949 | 1-cBu-CH(CH$_2$CH$_3$) | 2,6-diMeO-pyrid-3-yl |
| 950 | 1-cBu-CH(CH$_2$CH$_2$CH$_3$) | 2,6-diMeO-pyrid-3-yl |
| 951 | 1-cBu-CH(CH$_2$OCH$_3$) | 2,6-diMeO-pyrid-3-yl |
| 952 | 1-cBu-CH(CH$_2$CH$_2$OCH$_3$) | 2,6-diMeO-pyrid-3-yl |
| 953 | (cPr)$_2$CH | 2,6-diCH$_3$-pyrid-3-yl |
| 954 | phenyl(cPr)CH | 2,6-diCH$_3$-pyrid-3-yl |
| 955 | 2-furanyl(cPr)CH | 2,6-diCH$_3$-pyrid-3-yl |
| 956 | 3-furan(cPr)CH | 2,6-diCH$_3$-pyrid-3-yl |
| 957 | 2-thienyl(cPr)CH | 2,6-diCH$_3$-pyrid-3-yl |
| 958 | 3-thienyl(cPr)CH | 2,6-diCH$_3$-pyrid-3-yl |
| 959 | 2-isoxazolyl(cPr)CH | 2,6-diCH$_3$-pyrid-3-yl |
| 960 | 2-(5-CH$_3$-furanyl)(cPr)CH | 2,6-diCH$_3$-pyrid-3-yl |
| 961 | 2-(4-CH$_3$-isoxazolyl)(cPr)CH | 2,6-diCH$_3$-pyrid-3-yl |
| 962 | cPr-CH(CH$_3$) | 2,6-diCH$_3$-pyrid-3-yl |
| 963 | 1-cPr-CH(CH$_2$CH$_3$) | 2,6-diCH$_3$-pyrid-3-yl |
| 964 | 1-cPr-CH(CH$_2$CH$_2$CH$_3$) | 2,6-diCH$_3$-pyrid-3-yl |
| 965 | 1-cPr-CH(CH$_2$OCH$_3$) | 2,6-diCH$_3$-pyrid-3-yl |
| 966 | 1-cPr-CH(CH$_2$CH$_2$OCH$_3$) | 2,6-diCH$_3$-pyrid-3-yl |
| 967 | (cBu)$_2$CH | 2,6-diCH$_3$-pyrid-3-yl |
| 968 | phenyl(cBu)CH | 2,6-diCH$_3$-pyrid-3-yl |
| 969 | 2-furanyl(cBu)CH | 2,6-diCH$_3$-pyrid-3-yl |
| 970 | 3-furan(cBu)CH | 2,6-diCH$_3$-pyrid-3-yl |
| 971 | 2-thienyl(cBu)CH | 2,6-diCH$_3$-pyrid-3-yl |
| 972 | 3-thienyl(cBu)CH | 2,6-diCH$_3$-pyrid-3-yl |
| 973 | 2-isoxazolyl(cBu)CH | 2,6-diCH$_3$-pyrid-3-yl |
| 974 | 2-(5-CH$_3$-furanyl)(cBu)CH | 2,6-diCH$_3$-pyrid-3-yl |
| 975 | 2-(4-CH$_3$-isoxazolyl)(cBu)CH | 2,6-diCH$_3$-pyrid-3-yl |
| 976 | cBu-CH(CH$_3$) | 2,6-diCH$_3$-pyrid-3-yl |
| 977 | 1-cBu-CH(CH$_2$CH$_3$) | 2,6-diCH$_3$-pyrid-3-yl |
| 978 | 1-cBu-CH(CH$_2$CH$_2$CH$_3$) | 2,6-diCH$_3$-pyrid-3-yl |
| 979 | 1-cBu-CH(CH$_2$OCH$_3$) | 2,6-diCH$_3$-pyrid-3-yl |
| 980 | 1-cBu-CH(CH$_2$CH$_2$OCH$_3$) | 2,6-diCH$_3$-pyrid-3-yl |
| 981 | (cPr)$_2$CH | 2-CH$_3$-6-MeO-pyrid-3-yl |
| 982 | phenyl(cPr)CH | 2-CH$_3$-6-MeO-pyrid-3-yl |
| 983 | 2-furanyl(cPr)CH | 2-CH$_3$-6-MeO-pyrid-3-yl |
| 984 | 3-furan(cPr)CH | 2-CH$_3$-6-MeO-pyrid-3-yl |
| 985 | 2-thienyl(cPr)CH | 2-CH$_3$-6-MeO-pyrid-3-yl |
| 986 | 3-thienyl(cPr)CH | 2-CH$_3$-6-MeO-pyrid-3-yl |
| 987 | 2-isoxazolyl(cPr)CH | 2-CH$_3$-6-MeO-pyrid-3-yl |
| 988 | 2-(5-CH$_3$-furanyl)(cPr)CH | 2-CH$_3$-6-MeO-pyrid-3-yl |
| 989 | 2-(4-CH$_3$-isoxazolyl)(cPr)CH | 2-CH$_3$-6-MeO-pyrid-3-yl |
| 990 | cPr-CH(CH$_3$) | 2-CH$_3$-6-MeO-pyrid-3-yl |
| 991 | 1-cPr-CH(CH$_2$CH$_3$) | 2-CH$_3$-6-MeO-pyrid-3-yl |
| 992 | 1-cPr-CH(CH$_2$CH$_2$CH$_3$) | 2-CH$_3$-6-MeO-pyrid-3-yl |
| 993 | 1-cPr-CH(CH$_2$OCH$_3$) | 2-CH$_3$-6-MeO-pyrid-3-yl |
| 994 | 1-cPr-CH(CH$_2$CH$_2$OCH$_3$) | 2-CH$_3$-6-MeO-pyrid-3-yl |
| 995 | (cBu)$_2$CH | 2-CH$_3$-6-MeO-pyrid-3-yl |
| 996 | phenyl(cBu)CH | 2-CH$_3$-6-MeO-pyrid-3-yl |
| 997 | 2-furanyl(cBu)CH | 2-CH$_3$-6-MeO-pyrid-3-yl |
| 998 | 3-furan(cBu)CH | 2-CH$_3$-6-MeO-pyrid-3-yl |
| 999 | 2-thienyl(cBu)CH | 2-CH$_3$-6-MeO-pyrid-3-yl |
| 1000 | 3-thienyl(cBu)CH | 2-CH$_3$-6-MeO-pyrid-3-yl |
| 1001 | 2-isoxazolyl(cBu)CH | 2-CH$_3$-6-MeO-pyrid-3-yl |
| 1002 | 2-(5-CH$_3$-furanyl)(cBu)CH | 2-CH$_3$-6-MeO-pyrid-3-yl |
| 1003 | 2-(4-CH$_3$-isoxazolyl)(cBu)CH | 2-CH$_3$-6-MeO-pyrid-3-yl |
| 1004 | cBu-CH(CH$_3$) | 2-CH$_3$-6-MeO-pyrid-3-yl |
| 1005 | 1-cBu-CH(CH$_2$CH$_3$) | 2-CH$_3$-6-MeO-pyrid-3-yl |
| 1006 | 1-cBu-CH(CH$_2$CH$_2$CH$_3$) | 2-CH$_3$-6-MeO-pyrid-3-yl |
| 1007 | 1-cBu-CH(CH$_2$OCH$_3$) | 2-CH$_3$-6-MeO-pyrid-3-yl |
| 1008 | 1-cBu-CH(CH$_2$CH$_2$OCH$_3$) | 2-CH$_3$-6-MeO-pyrid-3-yl |
| 1009 | (cPr)$_2$CH | 4-CH$_3$-6-MeO-pyrid-3-yl |
| 1010 | phenyl(cPr)CH | 4-CH$_3$-6-MeO-pyrid-3-yl |
| 1011 | 2-furanyl(cPr)CH | 4-CH$_3$-6-MeO-pyrid-3-yl |
| 1012 | 3-furan(cPr)CH | 4-CH$_3$-6-MeO-pyrid-3-yl |
| 1013 | 2-thienyl(cPr)CH | 4-CH$_3$-6-MeO-pyrid-3-yl |
| 1014 | 3-thienyl(cPr)CH | 4-CH$_3$-6-MeO-pyrid-3-yl |
| 1015 | 2-isoxazolyl(cPr)CH | 4-CH$_3$-6-MeO-pyrid-3-yl |
| 1016 | 2-(5-CH$_3$-furanyl)(cPr)CH | 4-CH$_3$-6-MeO-pyrid-3-yl |
| 1017 | 2-(4-CH$_3$-isoxazolyl)(cPr)CH | 4-CH$_3$-6-MeO-pyrid-3-yl |
| 1018 | cPr-CH(CH$_3$) | 4-CH$_3$-6-MeO-pyrid-3-yl |
| 1019 | 1-cPr-CH(CH$_2$CH$_3$) | 4-CH$_3$-6-MeO-pyrid-3-yl |
| 1020 | 1-cPr-CH(CH$_2$CH$_2$CH$_3$) | 4-CH$_3$-6-MeO-pyrid-3-yl |
| 1021 | 1-cPr-CH(CH$_2$OCH$_3$) | 4-CH$_3$-6-MeO-pyrid-3-yl |
| 1022 | 1-cPr-CH(CH$_2$CH$_2$OCH$_3$) | 4-CH$_3$-6-MeO-pyrid-3-yl |
| 1023 | (cBu)$_2$CH | 4-CH$_3$-6-MeO-pyrid-3-yl |
| 1024 | phenyl(cBu)CH | 4-CH$_3$-6-MeO-pyrid-3-yl |
| 1025 | 2-furanyl(cBu)CH | 4-CH$_3$-6-MeO-pyrid-3-yl |
| 1026 | 3-furan(cBu)CH | 4-CH$_3$-6-MeO-pyrid-3-yl |
| 1027 | 2-thienyl(cBu)CH | 4-CH$_3$-6-MeO-pyrid-3-yl |
| 1028 | 3-thienyl(cBu)CH | 4-CH$_3$-6-MeO-pyrid-3-yl |
| 1029 | 2-isoxazolyl(cBu)CH | 4-CH$_3$-6-MeO-pyrid-3-yl |
| 1030 | 2-(5-CH$_3$-furanyl)(cBu)CH | 4-CH$_3$-6-MeO-pyrid-3-yl |
| 1031 | 2-(4-CH$_3$-isoxazolyl)(cBu)CH | 4-CH$_3$-6-MeO-pyrid-3-yl |
| 1032 | cBu-CH(CH$_3$) | 4-CH$_3$-6-MeO-pyrid-3-yl |
| 1033 | 1-cBu-CH(CH$_2$CH$_3$) | 4-CH$_3$-6-MeO-pyrid-3-yl |
| 1034 | 1-cBu-CH(CH$_2$CH$_2$CH$_3$) | 4-CH$_3$-6-MeO-pyrid-3-yl |
| 1035 | 1-cBu-CH(CH$_2$OCH$_3$) | 4-CH$_3$-6-MeO-pyrid-3-yl |
| 1036 | 1-cBu-CH(CH$_2$CH$_2$OCH$_3$) | 4-CH$_3$-6-MeO-pyrid-3-yl |
| 1037 | (cPr)$_2$CH | 4-CH$_3$-6-(CH$_3$)$_2$N-pyrid-3-yl |
| 1038 | phenyl(cPr)CH | 4-CH$_3$-6-(CH$_3$)$_2$N-pyrid-3-yl |
| 1039 | 2-furanyl(cPr)CH | 4-CH$_3$-6-(CH$_3$)$_2$N-pyrid-3-yl |
| 1040 | 3-furan(cPr)CH | 4-CH$_3$-6-(CH$_3$)$_2$N-pyrid-3-yl |
| 1041 | 2-thienyl(cPr)CH | 4-CH$_3$-6-(CH$_3$)$_2$N-pyrid-3-yl |
| 1042 | 3-thienyl(cPr)CH | 4-CH$_3$-6-(CH$_3$)$_2$N-pyrid-3-yl |
| 1043 | 2-isoxazolyl(cPr)CH | 4-CH$_3$-6-(CH$_3$)$_2$N-pyrid-3-yl |
| 1044 | 2-(5-CH$_3$-furanyl)(cPr)CH | 4-CH$_3$-6-(CH$_3$)$_2$N-pyrid-3-yl |
| 1045 | 2-(4-CH$_3$-isoxazolyl)(cPr)CH | 4-CH$_3$-6-(CH$_3$)$_2$N-pyrid-3-yl |
| 1046 | cPr-CH(CH$_3$) | 4-CH$_3$-6-(CH$_3$)$_2$N-pyrid-3-yl |
| 1047 | 1-cPr-CH(CH$_2$CH$_3$) | 4-CH$_3$-6-(CH$_3$)$_2$N-pyrid-3-yl |
| 1048 | 1-cPr-CH(CH$_2$CH$_2$CH$_3$) | 4-CH$_3$-6-(CH$_3$)$_2$N-pyrid-3-yl |
| 1049 | 1-cPr-CH(CH$_2$OCH$_3$) | 4-CH$_3$-6-(CH$_3$)$_2$N-pyrid-3-yl |
| 1050 | 1-cPr-CH(CH$_2$CH$_2$OCH$_3$) | 4-CH$_3$-6-(CH$_3$)$_2$N-pyrid-3-yl |
| 1051 | (cBu)$_2$CH | 4-CH$_3$-6-(CH$_3$)$_2$N-pyrid-3-yl |
| 1052 | phenyl(cBu)CH | 4-CH$_3$-6-(CH$_3$)$_2$N-pyrid-3-yl |
| 1053 | 2-furanyl(cBu)CH | 4-CH$_3$-6-(CH$_3$)$_2$N-pyrid-3-yl |
| 1054 | 3-furan(cBu)CH | 4-CH$_3$-6-(CH$_3$)$_2$N-pyrid-3-yl |
| 1055 | 2-thienyl(cBu)CH | 4-CH$_3$-6-(CH$_3$)$_2$N-pyrid-3-yl |
| 1056 | 3-thienyl(cBu)CH | 4-CH$_3$-6-(CH$_3$)$_2$N-pyrid-3-yl |
| 1057 | 2-isoxazolyl(cBu)CH | 4-CH$_3$-6-(CH$_3$)$_2$N-pyrid-3-yl |
| 1058 | 2-(5-CH$_3$-furanyl)(cBu)CH | 4-CH$_3$-6-(CH$_3$)$_2$N-pyrid-3-yl |
| 1059 | 2-(4-CH$_3$-isoxazolyl)(cBu)CH | 4-CH$_3$-6-(CH$_3$)$_2$N-pyrid-3-yl |
| 1060 | cBu-CH(CH$_3$) | 4-CH$_3$-6-(CH$_3$)$_2$N-pyrid-3-yl |
| 1061 | 1-cBu-CH(CH$_2$CH$_3$) | 4-CH$_3$-6-(CH$_3$)$_2$N-pyrid-3-yl |
| 1062 | 1-cBu-CH(CH$_2$CH$_2$CH$_3$) | 4-CH$_3$-6-(CH$_3$)$_2$N-pyrid-3-yl |
| 1063 | 1-cBu-CH(CH$_2$OCH$_3$) | 4-CH$_3$-6-(CH$_3$)$_2$N-pyrid-3-yl |
| 1064 | 1-cBu-CH(CH$_2$CH$_2$OCH$_3$) | 4-CH$_3$-6-(CH$_3$)$_2$N-pyrid-3-yl |

UTILITY

Compounds of this invention are expected to have utility in the treatment of inbalances associated with abnormal levels of CRF in patients suffering from depression, affective disorders, and/or anxiety.

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately $1\times10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer.

After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from $10^{-10}$–$10^{-5}$ M), 100 μl of $^{125}$I-ovine-CRF ($^{125}$I-o-CRF) (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980)], which provides Ki values for inhibition which are then used to assess biological activity. Alternatively, tissues and cells which naturally express CRF receptors can be employed in binding assays analogous to those described above.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6}$m) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) is added to each tube prior to separation. The separation of [$^{32}$p]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Dosage and Formulation

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula (I):

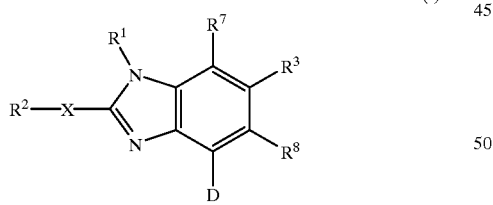

(I)

or a stereoisomer or pharmaceutically acceptable salt form thereof; wherein:

D is an aryl or heteroaryl group attached through an unsaturated carbon atom;

X is selected from the group consisting of CH—$R^9$, N—$R^{10}$, O, $S(O)_n$ and a bond;

n is 0, 1 or 2;

$R^1$ is selected from the group consisting of $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$—$C_{1-10}$ alkyl, —$SO_2$—$R^{1a}$, and —$SO_2$—$R^{1b}$;

$R^1$ is substituted with 1 or more substituents selected from the group consisting of —CN, —$S(O)_nR^{14b}$, —$COR^{13a}$, —$CO_2R^{13a}$, —$NR^{15a}COR^{13a}$, —$N(COR^{13a})_2$, —$NR^{15a}CONR^{13a}R^{16a}$, $NR^{15a}CO_2R^{14b}$, —$CONR^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —$S(O)_n$—, —$NR^{13a}$—, —$NCO_2R^{14b}$—, —$NCOR^{14b}$— and —$NSO_2R^{14b}$—, and wherein $N_4$ in 1-piperazinyl is substituted with 0–1 substituents selected from the group consisting of $R^{13a}$, $CO_2R^{14b}$, $COR^{14b}$ and $SO_2R^{14b}$;

$R^1$ is also substituted with 1–3 substituents independently selected at each occurrence from the group consisting of $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, $C_{1-4}$ alkoxy-$C_{1-4}$ alkyl and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl-$(CH_2)_2$— group;

$R^{1a}$ is aryl and is selected from the group consisting of phenyl, naphthyl, indanyl and indenyl, each $R^{1a}$ being substituted with 0–1 —$OR^{17}$ and 0–5 substituents independently selected at each occurrence from the group consisting of $C_{1-6}$ alkyl, $C_{3-6}$ cycloalkyl, Br, Cl, F, I, $C_{1-4}$ haloalkyl, —CN, nitro, SH, —$S(O)_nR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group consisting of pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group consisting of $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group consisting of $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group consisting of $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group consisting of $R^{13a}$, $CO_2R^{14b}$, $COR^{14b}$ and $SO_2R^{14b}$ and wherein any sulfur atom is monooxidized or dioxidized;

provided that $R^1$ is other than a —$(CH_2)_{1-4}$-aryl, —$(CH_2)_{1-4}$-heteroaryl, or —$(CH_2)_{1-4}$-heterocycle, wherein the aryl, heteroaryl, or heterocycle group is substituted or unsubstituted;

$R^2$ is $C_{1-4}$ alkyl, $C_{3-8}$ cycloalkyl, $C_{2-4}$ alkenyl, or $C_{2-4}$ alkynyl and is substituted with 0–3 substituents selected from the group consisting of —CN, hydroxy, halo and $C_{1-4}$ alkoxy;

alternatively $R^2$, in the case where X is a bond, —CN, $CF_3$ or $C_2F_5$;

$R^3$, $R^7$ and $R^8$ are independently selected at each occurrence from the group consisting of H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $(C_{1-4}$ alkyl$)_2$amino and phenyl, each phenyl is substituted with 0–3 groups selected from the group consisting of $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl$)_2$amino;

provided that when $R^1$ is unsubstituted $C_{1-10}$ alkyl, then $R^3$ is other than substituted or unsubstituted phenyl;

$R^9$ and $R^{10}$ are independently selected at each occurrence from the group consisting of H, $C_{1-4}$ alkyl, $C_{3-6}$ cycloalkyl-$C_{1-4}$ alkyl and $C_{3-8}$ cycloalkyl;

$R^{13}$ is selected from the group consisting of H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)—;

$R^{13a}$ and $R^{16a}$ are independently selected at each occurrence from the group consisting of H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group consisting of $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, benzyl being substituted on the aryl moiety with 0–1 substituents selected from the group consisting of $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group consisting of $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group consisting of $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group consisting of $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group consisting of H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group consisting of $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group consisting of H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group consisting of H, $C_{1-6}$ alkyl, $C_{3-10}$ cycloalkyl, $C_{3-6}$-cycloalkyl-$C_{1-6}$ alkyl, $C_{1-2}$ alkoxy-$C_{1-2}$ alkyl, $C_{1-4}$ haloalkyl, $R^{14}S(O)_n$-$C_{1-4}$ alkyl, and $R^{17b}R^{19b}N$—$C_{2-4}$ alkyl;

$R^{18}$ and $R^{19}$ are independently selected at each occurrence from the group consisting of H, $C_{1-6}$ alkyl, $C_{3-6}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^9$ moiety, $R^{17}$ and $R^{19}$ taken together form 1-pyrrolidinyl, 1-morpholinyl, 1piperidinyl or 1-piperazinyl, wherein $N_4$ in 1-piperazinyl is substituted with 0–1 substituents selected from the group consisting of $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group consisting of $R^{13}$, $CO_2R^{14}$, $COR^{14}$ and $SO_2R^{14}$;

$R^{17a}$ and $R^{19a}$ are independently selected at each occurrence from the group consisting of H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group consisting of phenyl, naphthyl, indanyl and indenyl, each aryl being substituted with 0–5 substituents independently selected at each occurrence from the group consisting of $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_n$$R^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group consisting of $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl;

heteroaryl is independently selected at each occurrence from the group consisting of pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group consisting of $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group consisting of $R^{15}$, $CO_2R^{14a}$, $COR^{14a}$ and $SO_2R^{14a}$; and, provided that when D is imidazole or triazole, $R^1$ is other than unsubstituted $C_{1-6}$ linear or branched alkyl or $C_{3-6}$ cycloalkyl.

2. A compound according to claim 1, wherein:
$R^1$ is $C_{3-8}$ cycloalkyl or $C_{3-6}$ cycloalkyl-$C_{1-6}$ alkyl.

3. A compound according to claim 1, wherein:
D is a heteroaryl group attached through an unsaturated carbon atom.

4. A compound according to claim 1, wherein:
D is a phenyl group substituted with 3–5 substituents independently selected at each occurrence from the group consisting of $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_n$$R^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, —$CONR^{17}R^{19}$ and up to 1 phenyl, each phenyl substituent being substituted with 0–4 substituents selected from the group consisting of $C_{1-3}$ alkyl, $C_{1-3}$ alkoxy, Br, Cl, F, I, —CN, dimethylamino, $CF_3$, $C_2F_5$, $OCF3$, $SO_2Me$ and acetyl.

5. A compound according to claim 1, wherein:

$R^1$ is $C_{1-10}$ alkyl; and $R^1$ is substituted with 1–3 substituents selected from the group consisting of $R^{1a}$, $R^{1b}$, $R^{1c}$, $C_{2-8}$ alkenyl, $C_{2-8}$ alkynyl, Br, Cl, F, I, $C_{1-4}$ haloalkyl, —$OR^{13a}$, —$NR^{13a}R^{16a}$, —CN, —$S(O)_nR^{14b}$, —$COR^{13a}$, —$CO_2R^{13a}$, —$NR^{15a}COR^{13a}$, $N(COR^{13a})_2$, $NR^{15a}CONR^{13a}R^{16a}$, —$NR^{15a}CO_2R^{14b}$, —$CONR^{13a}R^{16a}$, 1-morpholinyl, 1-piperidinyl, 1-piperazinyl wherein the $N_4$ in the 1-piperazinyl is substituted with 0–1 substituents selected from the group consisting of $R^{13a}$, $CO_2R^{14b}$, $COR^{14b}$ and $SO_2R^{14b}$; $C_{3-8}$ cycloalkyl wherein 0–1 carbon atoms in the $C_{4-8}$ cycloalkyl is replaced by a group selected from the group consisting of —O—, —$S(O)_n$—, —$NR^{13a}$, —$NCO_2R^{14b}$—, —$NCOR^{14b}$— and —$NSO_2R^{14b}$—; and $C_{3-8}$ cycloalkyl wherein the $C_{3-8}$ cycloalkyl is substituted with 0–1 $R^9$, and 0–1 carbons in the $C_{3-8}$ cycloalkyl is replaced by —O—.

6. A compound according to claim 1, wherein the compound is selected from:

1-(1,1-Dicyclopropyl)methyl-2-ethyl-4-(2,4,5-trichlorophenyl)-1H-benzimidazole, 1-(1,1-Dicyclopropyl)methyl-2-methoxy-4-(2,4,5-trichlorophenyl)-1H-benzimidazole, 1-(1-cyclopropyl)propyl-2-ethyl-4-(2,4,5-trichlorophenyl)-1H-benzimidazole, 1-cyclopentyl-2-ethyl-4-(2,4,5-trichlorophenyl)-1H-benzimidazole, 1-cyclopentyl-2-ethyl-4-(2,4 ,5-trichlorophenyl)-6-methyl-1H-benzimidazole, 1-(1-phenyl)propyl-2-ethyl-4-(2,4,5-trichlorophenyl)-1H-benzimidazole, 1-(1,1-diphenyl)methyl-2-ethyl-4-(2,4,5-trichlorophenyl)-1H-benzimidazole, 1-cyclopentyl-2-ethyl-4-(2,4,6-trimethylphenyl)benzimidazole, 1-(2-methyl)cyclopentyl-2-ethyl-4-(2,4,6-trimethylphenyl)-1H-benzimidazole, 1-(1,1-dicyclopropyl)methyl-2-ethyl-4-(2,4,6-trichlorophenyl)-1H-benzimidazole, 1-(1,1-dicyclopropyl)methyl-2-ethyl-4-(2,4-dichlorophenyl)-1H-benzimidazole, 1-(1,1-dicyclopropyl) methyl-2-ethyl-4-(2-methyl-4-methoxyphenyl)-1H-benzimidazole, 1-(1-cyclopropyl)butyl-2-ethyl-4-(2-methyl-4-methoxyphenyl)-1H-benzimidazole, 1-cyclopentyl-2-ethyl-4-(2,4,6-trimethyl-3-pyridyl)-1H-benzimidazole.

7. A pharmaceutical composition comprising a pharmaceutically acceptable carrier and a therapeutically effective amount of the compound of claim 1.

8. A method of treating a subject afflicted with affective disorder, anxiety or depression which comprises administering to the subject the pharmaceutical composition of claim 6.

* * * * *